US012723232B2

(12) United States Patent
Nakagiri et al.

(10) Patent No.: US 12,723,232 B2
(45) Date of Patent: Sep. 1, 2026

(54) METHOD FOR PREPARING SKIN-DERIVED PLURIPOTENT PRECURSOR CELLS

(71) Applicants: KAO CORPORATION, Tokyo (JP); OSAKA UNIVERSITY, Suita (JP)

(72) Inventors: Yoriko Nakagiri, Utsunomiya (JP); Kiyotoshi Sekiguchi, Suita (JP)

(73) Assignees: KAO CORPORATION, Tokyo (JP); OSAKA UNIVERSITY, Suita (JP)

( * ) Notice: Subject to any disclaimer, the term of this patent is extended or adjusted under 35 U.S.C. 154(b) by 898 days.

(21) Appl. No.: 17/633,082

(22) PCT Filed: Aug. 4, 2020

(86) PCT No.: PCT/JP2020/029855
§ 371 (c)(1),
(2) Date: Feb. 4, 2022

(87) PCT Pub. No.: WO2021/025027
PCT Pub. Date: Feb. 11, 2021

(65) Prior Publication Data

US 2022/0340868 A1 Oct. 27, 2022

(30) Foreign Application Priority Data

Aug. 6, 2019 (JP) ................................ 2019-144899

(51) Int. Cl.
*C12N 5/071* (2010.01)

(52) U.S. Cl.
CPC .......... *C12N 5/063* (2013.01); *C12N 2501/11* (2013.01); *C12N 2501/115* (2013.01); *C12N 2501/415* (2013.01); *C12N 2501/998* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 8,877,493 | B2 | 11/2014 | Sekiguchi et al. |
| 10,000,554 | B2 | 6/2018 | Sekiguchi et al. |
| 10,287,541 | B2 | 5/2019 | Sekiguchi et al. |
| 2012/0220031 | A1 | 8/2012 | Sekiguchi et al. |
| 2014/0127806 | A1 | 5/2014 | Sekiguchi et al. |
| 2017/0044495 | A1 | 2/2017 | Nakagiri |
| 2019/0211305 | A1 | 7/2019 | Eto et al. |
| 2019/0276804 | A1 | 9/2019 | Sekiguchi et al. |

FOREIGN PATENT DOCUMENTS

| | | | | |
|---|---|---|---|---|
| CN | 106167790 | A | 11/2016 | |
| JP | 2011-78370 | A | 4/2011 | |
| JP | WO 2012/137970 | A1 | 10/2012 | |
| JP | 2015-213495 | A | 12/2015 | |
| WO | WO-2012137970 | A1 * | 10/2012 | ............ C07K 14/78 |
| WO | WO 2018/038242 | A1 | 3/2018 | |
| WO | WO 2018/088501 | A1 | 5/2018 | |
| WO | WO 2018/143312 | A1 | 8/2018 | |

OTHER PUBLICATIONS

Nakagawa, Masato, et al. "A novel efficient feeder-free culture system for the derivation of human induced pluripotent stem cells." Scientific reports 4.1 (2014): 3594. (Year: 2014).*

Sugiyama-Nakagiri, Yoriko, Tsutomu Fujimura, and Shigeru Moriwaki. "Induction of skin-derived precursor cells from human induced pluripotent stem cells." PloS one 11.12 (2016): e0168451. (Year: 2016).*

Partial Supplementary European Search Report issued Jul. 5, 2023 in European Patent Application No. 20849572.1, 16 pages.

Sugiyama-Nakagiri et al., "Induction of Skin-Derived Precursor Cells from Human Induced Pluripotent Stem Cells", PLOS ONE, vol. 11, No. 12, Dec. 19, 2016, pp. 1-13, XP093055708.

Shibata et al., "Selective Laminin-Directed Differentiation of Human Induced Pluripotent Stem Cells into Distinct Ocular Lineages", Cell Reports, vol. 25, No. 6, Nov. 1, 2018, pp. 1668-1679 (Total pages 18), XP055650022.

International Search Report issued Oct. 6, 2020 in PCT/JP2020/029855 (submitting English translation only), 3 pages.

Jean G. Toma, et al., "Isolation of Multipotent Adult Stem Cells from the Dermis of Mammalian Skin" Nature Cell Biology, vol. 3, Sep. 2001, pp. 778-784.

Jeffrey Biernaskie, et al., "SKPs Derive from Hair Follicle Precursors and Exhibit Properties of Adult Dermal Stem Cells" Cell Stem Cell, vol. 5, Dec. 4, 2009, pp. 610-623.

Rebecca P. Hill, et al., "Generation and Characterization of Multipotent Stem Cells from Established Dermal Cultures" PLoS One, vol. 7, Issue 11, Nov. 2012, e50742, pp. 1-10.

Taniguchi, Yukimasa, et al., "Development of Cell Culture Substrate for Regenerative Medicine", Biotechnology, vol. 96, No. 6, 2018, pp. 328-332 (with unedited computer generated English translation).

Lee, Gabsang. et al., "Derivation of Neural Crest Cells from Human Pluripotent Stem Cells" Nature Protocols, vol. 5, No. 4, 2010, pp. 688-701 and cover pages.

(Continued)

*Primary Examiner* — Tracy Vivlemore
*Assistant Examiner* — Fatimah Khalaf Matalkah
(74) *Attorney, Agent, or Firm* — Oblon, McClelland, Maier & Neustadt, L.L.P.

(57) ABSTRACT

The present invention relates to improvement of the yield of skin-derived pluripotent precursor cells in induction of differentiation of stem cells to skin-derived pluripotent precursor cells. The present invention provides a method for preparing skin-derived pluripotent precursor cell comprising culturing a neural crest stem cells in the presence of at least one selected from the group consisting of laminin and a fragment thereof to differentiate the cells to skin-derived pluripotent precursor cells, wherein the laminin is at least one selected from the group consisting of laminin 111, laminin 121, laminin 332, laminin 421, laminin 511, laminin 521, and a variant thereof.

10 Claims, 6 Drawing Sheets

Specification includes a Sequence Listing.

(56) References Cited

OTHER PUBLICATIONS

Extended European Search Report issued Sep. 21, 2023 in European Patent Application No. 20849572.1, 19 pages.

Lee, G., et al., "Isolation and directed differentiation of neural crest stem cells derived from human embryonic stem cells", Nature Biotechnology, vol. 25, No. 12, Dec. 1, 2007, XP002659606, pp. 1468-1475.

Higuchi, A., et al., "Polymeric design of cell culture materials that guide the differentiation of human pluripotent stem cells", Progress in Polymer Science, vol. 65, Sep. 13, 2016, XP029897007, pp. 83-126.

Miyazaki, T. et al., Laminin E8 fragments support efficient adhesion and expansion of dissociated human pluripotent stem cells. Nature Communications, vol. 3, No. 1236, Dec. 4, 2012, 10 pages, XP055055638.

Ohta et al., Laminin-guided highly efficient endothelial commitment from huma pluripotent stem cells. Scientific Reports, 6:35680; DOI:10.1038/srep35680, pp. 1-12, Published Nov. 2, 2016 (12 pages).

* cited by examiner

METHOD FOR PREPARING SKIN-DERIVED PLURIPOTENT PRECURSOR CELLS

FIELD OF THE INVENTION

The present invention relates to a method for preparing skin-derived pluripotent precursor cells.

BACKGROUND OF THE INVENTION

In recent years, regenerative medicine using artificially cultured cells and tissues has been attracting attention. For example, treatment of alopecia by regenerating hair follicles is important to improve the quality of life (QOL) of individuals in view of their appearance (social aspect), health, and so forth.

One of cell sources used for artificial culture of cells and tissues is skin-derived pluripotent precursor cells (skin-derived precursor cells; hereinafter also referred to as "SKPs" in the present specification). SKPs are present in the hair papilla and are capable of differentiating into nerve cells, glial cells (neuroglial cells), smooth muscle cells, adipocytes, bone cells, dermal fibroblasts, hair papilla cells, and the like. Additionally, SKPs perform important functions in maintenance of dermal environment, repair of tissues, formation of hair follicles, and the like (refer to Non-Patent Literatures 1 and 2).

Currently, various clinical and nonclinical studies are ongoing in the field of regenerative medicine. To conduct these studies, there are needs for development of methods for obtaining a large amount of SKPs efficiently. Examples of the methods for obtaining SKPs which have been reported so far include a method of collecting SKPs from human or non-human animal tissues as a floating cell mass and culturing the cells (for example, refer to Non-Patent Literature 1) and a method of preparing SKPs using cultured adherent cells from human or non-human animal tissues (for example, refer to Non-Patent Literature 3). Patent Literature 1 discloses a method for preparing SKPs including culturing neural crest stem cells derived from human-derived pluripotent stem cells in a differentiation-inducing medium containing a Wnt signaling agonist to differentiate the cells to SKPs.

Pluripotent cells such as ES cells and iPS cells are usually cultured in coexistence with feeder cells. In contrast, artificially cultured cells used in human regenerative medicine are cultured preferably under a feeder-free condition, in which feeder cells are not used, more preferably under a xeno-free condition, in which xenogeneic components are not contained. A method of culturing pluripotent cells under a feeder-free condition using cell adhesion molecules instead of feeder cells has been developed. Patent Literature 2 discloses a method of culturing human pluripotent stem cells using a culture substrate coated with laminin 511 E8 fragment or laminin 332 E8 fragment. Patent Literature 3 discloses a method of culturing mammal cells including culturing stem cells, such as ES cells and iPS cells, in the presence of modified laminin containing laminin or a laminin fragment which is bound to a fragment containing a binding site for a growth factor such as heparan sulfate proteoglycan. Patent Literature 4 discloses a method of culturing pluripotent stem cells including bringing laminin 421 and laminin 121 or a fragment thereof into contact with pluripotent stem cells. Patent Literature 5 discloses a method of inducing differentiation of pluripotent stem cells including bringing a conjugate ligated with laminin E8 fragment and a fragment containing a growth factor binding site of heparan sulfate proteoglycan into contact with human pluripotent stem cells.

(Patent Literature 1) JP-A-2015-213495
(Patent Literature 2) JP-A-2011-078370
(Patent Literature 3) WO 2012/137970
(Patent Literature 4) WO 2018/038242
(Patent Literature 5) WO 2018/088501
(Non-Patent Literature 1) Nature Cell Biology, 2001, 3:778-784
(Non-Patent Literature 2) Cell Stem Cell, 2009, 5:610-623
(Non-Patent Literature 3) PLoS One, 2012, 7(11):e50742

SUMMARY OF THE INVENTION

In one embodiment, the present invention provides a method for preparing skin-derived pluripotent precursor cells, comprising culturing neural crest stem cells in the presence of at least one selected from the group consisting of laminin and a fragment thereof to differentiate the cells to skin-derived pluripotent precursor cells, wherein the laminin is at least one selected from the group consisting of laminin 111, laminin 121, laminin 332, laminin 421, laminin 511, laminin 521, and a variant thereof.

In another embodiment, the present invention provides a scaffolding material for culture for induction of differentiation of neural crest stem cells to pluripotent precursor cells, comprising at least one selected from the group consisting of laminin and a fragment thereof as an active ingredient, wherein the laminin is at least one selected from the group consisting of laminin 111, laminin 121, laminin 332, laminin 421, laminin 511, laminin 521, and a variant thereof.

In yet another embodiment, the present invention provides a method for preparing neural crest stem cells, comprising culturing pluripotent stem cells in the presence of at least one selected from the group consisting of laminin and a fragment thereof bound to perlecan or a fragment containing a growth factor binding site thereof to differentiate the cells to neural crest stem cells, wherein the laminin is at least one selected from the group consisting of laminin 111, laminin 121, laminin 332, laminin 421, laminin 511, laminin 521, and a variant thereof.

In yet another embodiment, the present invention provides a scaffolding material for culture for induction of differentiation of pluripotent stem cells to neural crest stem cells comprising at least one selected from the group consisting of laminin and a fragment thereof bound to perlecan or a fragment containing a growth factor binding site thereof as an active ingredient, wherein the laminin is at least one selected from the group consisting of laminin 111, laminin 121, laminin 332, laminin 421, laminin 511, laminin 521, and a variant thereof.

DETAILED DESCRIPTION OF THE INVENTION

Figure 1:
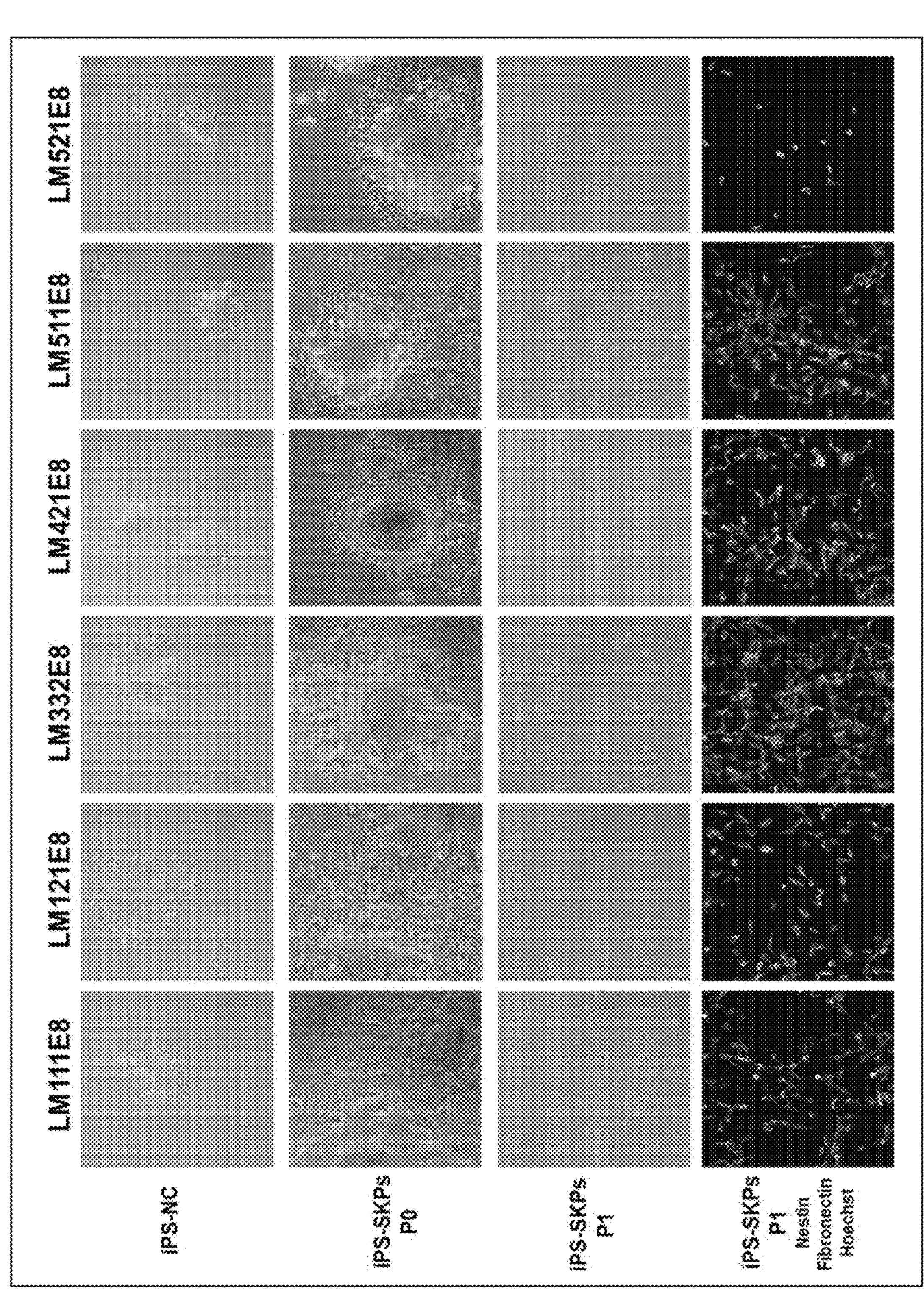
FIG. 1 shows induction of differentiation of NCS cells to SKPs in the presence of laminin fragments. iPS-NCS shows cells immediately before the initiation of induction of differentiation; iPS-SKPs P0 shows cells after four days of induction of differentiation; and iPS-SKPs P1 shows cells after subculture (all 40-fold magnifications). The lowermost row shows fluorescence staining images of nestin and fibronectin in iPS-SKPs P1 (50-fold magnifications).

All Patent Literatures, Non-Patent Literatures, and other publications cited in the present specification are incorporated by reference in entirety in the present specification.

As used herein, the term "pluripotent stem cells" refer to undifferentiated cells having pluripotency, which is an ability to differentiate into various tissues constituting an adult body, and self-renewal capacity. The pluripotent stem cells used in the present invention can be suitably selected, and specific examples of pluripotent stem cells include embryonic stem cells (hereinafter also referred to as "ES cells"), embryonal carcinoma cells (hereinafter also referred to as "EC cells"), embryonic germ stem cells (hereinafter also referred to as "EG cells"), and induced pluripotent stem cells (iPS cells). These cells may be prepared by a usual method, and commercially available cells may be used. The pluripotent stem cells used in the present invention are preferably ES cells or an iPS cells, more preferably iPS cells. The pluripotent stem cells used in the present invention may be any mammal-derived pluripotent stem cells and are preferably pluripotent stem cells derived from human, mouse, rat, bovine, swine, and non-human primates, more preferably human-derived pluripotent stem cells. Among them, human-derived ES cells and iPS cells are preferred, and human-derived iPS cells are more preferred.

As used herein, the term "skin-derived pluripotent precursor cells (skin-derived precursor cells; SKPs)" refer to undifferentiated cell having a self-renewal capacity and a capacity of differentiating to nerve cells, glia cells (e.g., microglia, astrocytes, oligodendrocytes, ependymal cells, Schwann cells, and satellite cells), smooth muscle cells, adipocytes, bone cells, dermal fibroblasts, hair papilla cells, or the like. SKPs can be identified on the basis of expression of a marker protein, such as nestin, fibronectin, or αSMA, and preferably on the basis of co-expression of nestin and fibronectin. Alternatively, SKPs can be identified on the basis of expression of a marker gene, such as Nestin gene, Snail gene, Slug gene, Sox9 gene, Dermo-1 gene, BMP-4 gene, and Wnt-5a gene.

As used herein, the term "neural crest stem cells" (hereinafter also referred to as "NCS cells") refer to pluripotent stem cells having a self-renewal capacity and pluripotency, which migrates from the back side of the neural tube to all over the body during the process of development of a vertebrate and contributes to formation of various tissues. Neural crest stem cells can be identified on the basis of expression of a known marker, such as paired box 6 (PAX6) and a nerve growth factor receptor (p75).

Expression of a marker protein or a marker gene in a cell can be detected according to a usual method. For example, expression of a marker protein in a cell can be detected by immunohistochemical staining, Western blot, ELISA, and the like, using an antibody against the marker protein. Additionally, expression of a marker gene in a cell can be detected by, for example, PCR, microarray, sequencing, and the like.

As used herein, the term "Wnt signaling" refers to a series of pathways which activate three pathways: the β-catenin pathway, the PCP pathway, and the $Ca^{2+}$ pathway, which are elicited by binding of a Wnt protein to a receptor thereof. Activation of Wnt signaling regulates various cell functions, such as cell proliferation and differentiation, organogenesis, and cell motility during early development. The term "Wnt signaling" as used herein preferably refers to the β-catenin pathway (canonical cascade). In this pathway, β-catenin is stabilized by binding of a Wnt protein to a receptor thereof and migrates into the nucleus to act as a transcription factor, whereby activating gene transcription. Additionally, β-catenin also appears to be involved in cell adhesion. Meanwhile, when the β-catenin pathway is turned off, β-catenin forms a degradation complex consisting of a plurality of proteins and is degraded after phosphorylation by glycogen synthase 3 (GSK-3) and casein kinase 1α (CK1α), which are serine/threonine kinases, in the complex, so that the intracellular level of β-catenin should be maintained low.

As used herein, the term "Wnt signaling agonist" refers to a factor activating the above-described Wnt signaling, preferably a factor activating the above-described β-catenin pathway (canonical cascade). Examples of a factor activating the β-catenin pathway include a factor activating gene transcription by inhibiting a β-catenin kinase, such as GSK-3, to promote nuclear translocation of β-catenin. Therefore, a GSK-3 inhibitor, which is a β-catenin kinase inhibitor, is included in the examples of a factor activating the β-catenin pathway.

Laminin is one of main extracellular matrices and a protein involved in adhesion, migration, proliferation, and the like of cells. Laminin is a heterotrimer molecule having three different subunits (α chain, β chain, and γ chain). So far, five different α chains (α1, α2, α3, α4, and α5), three different β chains (β1, β2, and β3), and three different γ chains (γ1, γ2, and γ3) have been found, and there are many laminin isoforms formed by different combinations thereof.

The laminin family members are designated according to the types of subunits. For example, laminin consisting of an α5 chain, a β1 chain, and a γ1 chain is referred to as laminin 511.

As used herein, the term "laminin E8 fragment" (hereinafter also simply referred to as "laminin E8") refers to a fragment composed of a trimer consisting of a C-terminal fragment of a laminin α chain from which spherical domains 4 and 5 have been removed (hereinafter referred to as "α chain E8"), a C-terminal fragment of a β chain (hereinafter referred to as "β chain E8"), and a C-terminal fragment of a γ chain (hereinafter referred to as "γ chain E8"). The molecular weight of the trimer is approximately 150 to approximately 170 kDa. Usually, a chain E8 consists of approximately 770 amino acids, and approximately 230 amino acids on the N-terminal side are involved in formation of the trimer. Usually, β chain E8 consists of approximately 220 to approximately 230 amino acids. Usually, γ chain E8 consists of approximately 240 to approximately 250 amino acids, and the third glutamic acid residue from the C-terminus is essential for the integrin binding activity of laminin E8 (refer to The Journal of Biological Chemistry, 2007, 282:11144-11154).

The amino acid sequences of an α chain, a β chain, and a γ chain of mammal laminin and the nucleotide sequences of genes coding therefor can be obtained from known databases (e.g., GenBank [www.ncbi.nlm.nih.gov/genbank/]). Table 1 shows GenBank accession numbers of chains constituting human laminin. Laminin can be manufactured according to a known method such as, for example, a method for purifying laminin from cells with high expression of laminin or a method for manufacturing laminin as a recombinant protein. A laminin fragment can be manufactured according to a known method such as a method for digesting full-length laminin with a proteolytic enzyme or a method for allowing direct expression of a laminin fragment as a recombinant. Alternatively, commercial products of laminin or a fragment thereof can be purchased.

TABLE 1

| | Amino acid sequence | Nucleotide sequence |
|---|---|---|
| Human laminin α1 chain | NP_005550 | NM_005559 |
| Human laminin α2 chain | NP_000417 | NM_000426 |
| Human laminin α3 chain | NP_000218 | NM_000227 |
| Human laminin α4 chain | NP_002281 | NM_002290 |
| Human laminin α5 chain | NP_005551 | NM_005560 |
| Human laminin β1 chain | NP_002282 | NM_002291 |
| Human laminin β2 chain | NP_002283 | NM_002292 |
| Human laminin β3 chain | NP_000219 | NM_000228 |
| Human laminin γ1 chain | NP_002284 | NM_002293 |
| Human laminin γ2 chain | NP_005553 | NM_005562 |
| Human laminin γ3 chain | NP_006050 | NM_006059 |

Improvement of the yield of SKPs in induction of differentiation of neural crest stem cells to SKPs as described in Patent Literature 1 is desired. SKPs cultured under a feeder-free condition, which are suitable as a cell source for regenerative medicine, are desired.

The present inventors found that feeder-free cell culture is enabled by using a specific laminin species as a culture scaffolding material in a culture for induction of differentiation of neural crest stem cells to SKPs. Additionally, the present inventors found that differentiation of neural crest stem cells to SKPs is promoted under this culture condition, whereby improving the yield of SKPs.

According to the present invention, SKPs that can be differentiated to nerve cells, glia cells, smooth muscle cells, adipocytes, bone cells, hair papilla cells, and the like can be efficiently prepared. According to the present invention, induction of differentiations of pluripotent stem cells to neural crest stem cells and induction of differentiation of neural crest stem cells to SKPs under a feeder-free condition is enabled. Therefore, according to the present invention, SKPs preferable as a cell source for regenerative medicine can be provided.

In one embodiment, the present invention provides a method for preparing skin-derived pluripotent precursor cells (SKPs). In this method, differentiation of neural crest stem (NCS) cells to SKPs is induced. More specifically, the method includes culturing NCS cells in the presence of laminin and/or a fragment thereof to differentiate the cells to SKPs.

Examples of the laminin which can be used for the culture for induction of differentiation to SKPs include at least one selected from the group consisting of laminin 111 (α1β1γ1), laminin 121 (α1β2γ1), laminin 332 (α3β3γ2), laminin 421 (α4β2γ1), laminin 511 (α5β1γ1), and laminin 521 (α5β2γ1), preferably at least one selected from the group consisting of laminin 111, laminin 332, laminin 421, and laminin 511.

Either the laminin or a fragment thereof may be used, or combinations thereof may be used. Therefore, the laminin and/or a fragment thereof which can be used for the culture for induction of differentiation to SKPs can be preferably at least one selected from the group consisting of laminin 111, laminin 121, laminin 332, laminin 421, laminin 511, laminin 521, and a fragment thereof, more preferably at least one selected from the group consisting of laminin 111, laminin 332, laminin 421, laminin 511, and a fragment thereof.

Examples of the laminin fragment can be any laminin fragments having the same cell adhesion activity as the full-length proteins of the above-mentioned laminin species, and the molecular weight and structure thereof are not particularly limited. Preferred examples of the laminin fragment which can be used for culture for induction of differentiation to SKPs include fragments of the above-mentioned laminin species having an integrin binding activity, more preferred examples thereof include fragments containing an E8 fragment of the above-mentioned laminin species, and even more preferred examples include an E8 fragment of the above-mentioned laminin species.

The laminin and/or a fragment thereof which can be used for culture for induction of differentiation to SKPs may be either human-derived laminin and/or a fragment thereof or non-human mammal-derived laminin and/or a fragment thereof. The laminin and/or a fragment thereof are preferably laminin and/or a fragment thereof derived from the same species as that of SKPs to be prepared, more preferably human laminin and/or a fragment thereof.

The laminin and/or a fragment thereof which can be used for culture for induction of differentiation to SKPs are natural laminin and/or a fragment thereof, a variant thereof, or a combination thereof. Examples of a variant of the laminin and/or a fragment include a polypeptide consisting of an amino acid sentence of a parent natural laminin or a fragment thereof (e.g., laminin 111, laminin 121, laminin 332, laminin 421, laminin 511, and laminin 521, and a fragment thereof) but in which one or several amino acids are deleted, substituted, or added and having an integrin binding activity. Here, the term "several" may be, for example, two to ten, may be two to eight, may be two to six, and may be two to four. Therefore, as used herein, laminin encompasses natural laminin and a variant thereof. This is also applicable to a laminin fragment.

Furthermore, the laminin and/or a fragment thereof which can be used for culture for induction of differentiation to SKPs may be modified laminin and/or a fragment thereof obtained by further modification to the above described laminin and/or a fragment thereof. Examples of the modified laminin and/or a fragment thereof include the laminin and/or a fragment thereof bound to perlecan or a fragment containing a growth factor binding site thereof (also referred to as "perlecan-modified laminin/fragment" in the present specification) (refer to Patent Literatures 3 and 5). In view of efficiency in induction of differentiation to SKPs, the laminin and/or a fragment thereof which can be used for culture for induction of differentiation to SKPs in the present invention are preferably perlecan-modified laminin/fragment thereof. The perlecan or a fragment containing a growth factor binding site thereof used for the modification are preferably derived from the same species as that of the laminin or a fragment thereof, more preferably human perlecan (GeNBaNk:NP_005520, NM_005529) or a fragment containing a growth factor binding site thereof. Examples of the growth factor binding site of perlecan include perlecan domains I to III (e.g., a region of 22nd valine to 1676th proline from the N-terminus of the amino acid sequence of human perlecan) (The Journal of Biological Chemistry, 2003, 278:30106-30114), and domain I ($Gly^{25}$-$Pro^{196}$) are preferred among them. For example, the perlecan or a fragment containing a growth factor binding site thereof can be manufactured according to a known method such as, for example, a method for purifying the fragment from cells with high expression of the fragment or a method for manufacturing the fragment as a recombinant protein.

In the perlecan-modified laminin/fragment, the perlecan or a fragment containing a growth factor binding site thereof may be bound to at least any one site among the N-terminus of an $\alpha$ chain, the C-terminus of an $\alpha$ chain, the N-terminus of a $\beta$ chain, and the N-terminus of a $\gamma$ chain of laminin or a fragment thereof. Therefore, the perlecan-modified laminin/fragment can have one to four molecules of the perlecan or a fragment containing a growth factor binding site thereof. All of the molecules may be perlecan, all of them may be a perlecan fragment containing a growth factor binding site, or some of them may be perlecan and the others may be a perlecan fragment containing a growth factor binding site. In the perlecan-modified laminin or a fragment thereof used in the present invention, preferably one molecule of perlecan or a fragment containing a growth factor binding site thereof is bound to the C-terminus of an $\alpha$ chain of laminin or a fragment thereof, more preferably one molecule of a growth factor binding site of perlecan is bound to the C-terminus of an $\alpha$ chain of a laminin fragment. Preferred examples of laminin, a laminin fragment, perlecan, and growth factor binding sites thereof contained in the perlecan-modified laminin/fragment are as described above.

The perlecan-modified laminin/fragment can be prepared according to, for example, the procedure described in Patent Literature 3 using known gene recombination techniques. More specifically, a DNA coding for a fusion protein of perlecan or a fragment containing a growth factor binding site thereof and laminin or a fragment thereof is constructed by ligating a DNA coding for laminin or a fragment thereof and a DNA coding for perlecan or a fragment containing a growth factor binding site thereof. A target perlecan-modified laminin/fragment can be prepared by introducing a vector containing a DNA coding for the fusion protein into a host cell to express the protein. Alternatively, a target perlecan-modified laminin/fragment can be synthesized by chemically binding perlecan or a fragment containing a growth factor binding site thereof to an appropriate position of laminin or a fragment thereof.

The above-described laminins and/or a fragment thereof which can be used in the present invention may contain a sequence used for their construction, isolation, purification, or binding to perlecan or a fragment thereof, for example, a tag sequence, a linker sequence, or the like.

In the method for preparing SKPs of the present invention, NCS cells are cultured in the presence of the laminin and/or a fragment thereof to differentiate the cells to SKPs. In this step, the laminin and/or a fragment thereof are used as a culture scaffolding material when NCS cells are cultured to induce differentiation to SKPs. Therefore, the method of the present invention does not need to use feeder cells and enables culture under a feeder-free condition, unlike conventional methods for culturing to induce differentiation to SKPs.

NCS cells used in the method for preparing SKPs of the present invention can be prepared by a known method. For example, NCS cells can be prepared by collecting NCS cells from an early embryo and proliferating the cells as necessary, inducing differentiation of pluripotent stem cells, and the like. NCS cells used in the method of the present invention are preferably pluripotent stem cell-derived NCS cells, which are obtained by inducing differentiation of pluripotent stem cells, more preferably induced pluripotent stem (iPS) cell-derived NCS cells, which are obtained by inducing differentiation of induced pluripotent stem (iPS) cells.

Therefore, in one embodiment, the method for preparing SKPs of the present invention may further include a step of inducing differentiation of pluripotent stem cells to NCS cells to prepare pluripotent stem cell-derived NCS cells. In a preferred embodiment, the step of preparing pluripotent stem cell-derived NCS cells includes culturing pluripotent stem cells in the presence of laminin and/or a fragment thereof to differentiate the cells to NCS cells.

Furthermore, pluripotent stem cells may be pre-cultured before performing the above-described induction of differentiation to NCS cells, as necessary. The pre-culture is also preferably performed in the presence of laminin and/or a fragment thereof. Stem cells which maintain pluripotency after the pre-culture can be used to the induction of differentiation to NCS cells.

The types of laminin and/or a fragment thereof used in the step of preparing NCS cells are not particularly limited, and examples thereof include laminin and/or a fragment thereof which can be used for the above-described culture for induction of differentiation to SKPs; and laminin, a laminin fragment, and modified laminin used for culture of pluripotent stem cells described in Patent Literatures 2 to 5. Laminin and/or a fragment thereof used in this step can be preferably at least one selected from the group consisting of laminin and a fragment thereof which can be used for the above-described culture for induction of differentiation to SKPs. Laminin and/or a fragment thereof used in this step may be of the same types as laminin and/or a fragment thereof used for the above-described induction of differentiation of SKPs or of a different type. In a preferred embodiment, laminin and/or a fragment thereof used in the step of preparing NCS cells are perlecan-modified laminin/fragment which can be used for the above-described culture for induction of differentiation to SKPs. The efficiency of induction of differentiation to NCS cells can be improved by using perlecan-modified laminin/fragment. In a preferred embodiment of the present invention, pluripotent stem cells are cultured to differentiate the cells to NCS cells in the presence of perlecan-modified laminin/fragment which can be used for the above-described culture for induction of differentiation to SKPs, and then the NCS cells are continuously cultured to differentiate the NCS cells to SKPs.

In the step of preparing NCS cells, the laminin and/or a fragment thereof are used as a culture scaffolding material for culture for induction of differentiation of pluripotent stem cells to NCS cells. Therefore, unlike conventional methods of culturing pluripotent stem cells, feeder cells do not need to be used in this step, enabling feeder-free culture.

The pre-culture of pluripotent stem cells, the culture for induction of differentiation of pluripotent stem cells to NCS cells, and the culture for induction of differentiation of NCS cells to SKPs of the present invention are performed preferably ex vivo and do not include culture on or in a living human or animal body. Therefore, the laminin and/or a fragment thereof used as a culture scaffolding material in the present invention are used preferably ex vivo and are not used on or in a living human or animal body.

In the present invention, the laminin and/or a fragment thereof may be used in any method, as long as they function as a culture scaffolding. For example, cells may be cultured on a culture substrate containing the laminin and/or a fragment thereof. Examples of the culture substrate containing the laminin and/or a fragment thereof include a culture substrate having a coating containing the laminin and/or a fragment thereof (e.g., plate, mesh, and dish), and examples thereof include a culture substrate to which the laminin and/or a fragment thereof are adsorbed by applying a coating agent containing the laminin and/or a fragment thereof. The content of the laminin and/or a fragment thereof in such a culture substrate may be preferably 0.05 to 50 μg, more preferably 0.1 to 10 μg per $cm^2$ of an area of the culture substrate brought into contact with a culture. For example, the culture substrate may be coated with a coating agent containing preferably 0.05 to 50 μg, more preferably 0.1 to 10 μg of the laminin and/or a fragment thereof per $cm^2$ of a coated area to adsorb the laminin and/or a fragment thereof to the culture substrate.

Alternatively, in the present invention, cells may be cultured in a medium to which the laminin and/or a fragment thereof are added. When the laminin and/or a fragment thereof are added to the medium, the laminin and/or a fragment thereof may be added to the medium before seeding cells, or the laminin and/or a fragment thereof may be added to the medium together with cells. The content of the laminin and/or a fragment thereof in the medium can be adjusted preferably to 0.1 to 100 μg, more preferably 0.2 to 20 μg per mL of the medium as a final concentration.

The culture substrate, coating agent, and medium containing the laminin and/or a fragment thereof may contain a scaffolding material other than the laminin and/or a fragment thereof or a cell adhesion molecule. Examples of the scaffolding material or the cell adhesion molecule include gelatin, collagen, Matrigel, fibronectin, and poly-L-lysin.

Differentiation media commonly used to induce differentiation of stem cells can be used as any of media used for culture for induction of differentiation of NCS cells to SKPs and media used for culture for induction of differentiation of pluripotent stem cells to NCS cells. Maintenance media commonly used for maintenance culture of stem cells can be used for pre-culture of pluripotent stem cells. A base medium of these media can be selected suitably from base media commonly used for culture of stem cells, and a commercial product can also be used. Examples of the base medium include Minimum Essential Medium (MEM), Basal Medium Eagle (BME), Iscove's Modified Dulbecco's Medium (IMDM), Dulbecco's Modified Eagle's Medium (DMEM), Ham's medium, Roswell Park Memorial Institute (RPMI) medium, Fischer's medium, and mixed media thereof. Of these, DMEM/Ham's F12 medium (hereinafter also simply referred to as "DMEM/F12 medium") is preferred. For feeder-free culture, a base medium can be selected suitably from base media prepared for feeder-free culture of stem cells, or a commercial product can be used. Examples thereof include StemFit (registered trade name) AK02N (Ajinomoto Co., Inc.).

The medium may be a serum-containing medium, a serum-free medium, or a medium containing a serum substitute, and preferably a serum-free medium or a medium containing a serum substitute. The serum substitute is a composition containing components such as albumin, transferrin, fatty acid, collagen precursor, a trace element (e.g., zinc, selenium), and a nutritional factor (e.g., epidermal growth factor [EGF], and basic fibroblast growth factor [bFGF]), which are components contained in serum. Compositions of a serum substitute are not limited as long as it has an ability to proliferate cells. Specific examples thereof include B-27 (brand name) supplement, N2 supplement, and KnockOut Serum Replacement. Furthermore, as necessary, components commonly used for a stem cell medium, such as a vitamin, a buffer, an inorganic salt, an antibiotic (e.g., penicillin, kanamycin, streptomycin), and 2-mercaptoethanol, may be added to the medium. Preferably, the medium is a xeno-free medium not containing xenogeneic components derived from an organism of species different from that of cells to be cultured. Of note, a commercial product may be used as the medium as long as feeder-free, preferably xeno-free culture can be achieved.

The differentiation medium for culture for induction of differentiation of NCS cells to SKPs preferably contains at least one nutritional factor selected from the group consisting of serum substitutes, EGF, and bFGF, more preferably a serum substitute, EGF, and bFGF. Preferred serum substitutes are the above-described B-27 (brand name) supplement, N2 supplement, or KnockOut Serum Replacement, and B-27 (brand name) supplement is more preferred. These nutritional factors may be prepared according to a usual method, or a commercial product may be used. The content of the nutritional factors in the differentiation medium can be suitably selected depending on the culture condition, the type of a pluripotent stem cell to be used, the type of an inhibitor, and the like. For example, the concentration of the serum substitute in the medium is preferably 0.5 mass % or higher, more preferably 1 mass % or higher, and preferably 20 mass % or lower, more preferably 5 mass % or lower, or the concentration range is preferably from 0.5 to 20 mass %, more preferably from 1 to 5 mass %. For example, the concentrations of EGF and bFGF in the medium are preferably both 1 ng/mL or higher, more preferably 10 ng/mL or higher, and preferably 100 ng/mL or lower, more preferably 50 ng/mL or lower, or the concentration range is preferably from 1 to 100 ng/mL, more preferably from 10 to 50 ng/mL.

Furthermore, induction of differentiation of NCS cells to SKPs is promoted by adding a Wnt signaling agonist to the differentiation medium, resulting in improvement of the yield of SKPs. The Wnt signaling agonist used in the present invention is as defined above, and preferred examples thereof include the above-described factor activating the β-catenin pathway and a factor inhibiting intracellular degradation of β-catenin, such as GSK-3 inhibitor. GSK-3 inhibitor is preferred.

Examples of a GSK-3 inhibitor include an amino pyrimidine compound (e.g., GSK-3 inhibitor XVI, trade name CHIR99021; CAS 252917-06-9), a bis-indole (indirubin) compound (hereinafter also referred to as "BIO") [e.g., (2'Z,3'E)-6-bromoindirubin-3'-oxime; CAS 667463-62-9], an acetoxime compound of BIO (hereinafter also referred to as "BIO-acetoxime") [e.g., (2'Z,3'E)-6-bromoindirubin-3'-acetoxime], a thiadiazolidine (TDZD) compound (e.g., 4-benzyl-2-methyl-1,2,4-thiadiazolidine-3,5-dione), an oxothiadiazolidine-3-thione compound (e.g., 2,4-dibenzyl-5-oxothiadiazolidine-3-thione), a thienyl α-chloromethyl ketone compound (e.g., 2-chloro-1-(4,4-dibromo-thiophen-2-yl)-ethanone), a phenyl α-bromomethyl ketone compound (e.g., α-4-dibromoacetophenone), a thiazole-containing urea compound [e.g., N-(4-methoxybenzyl)-N'-(5-nitro-1,3-thiazol-2-yl)urea], 1H-pyrazolo[3,4-b]quinoxalin-3-amine [trade name: NSC693868 (CAS 40254-90-8)], (2,4-dichlorophenyl)-4-(1-methyl-1H-indol-3-yl)-1H-pyrrol-2,5-dione [trade name: SB216763 (CAS 280744-09-4)], 3-[(3-chloro-4-hydroxyphenyl)amino]-4-(2-nitrophenyl)-1H-pyrrol-2,5-dione [trade name: SB415286 (CAS 264218-23-7)], GSK-3β inhibitor XII [trade name: TWS119 (CAS 601514-19-6)], and a GSK-3β peptide inhibitor (e.g., H-KEAPPAPPQSpP-NH2). Of these, at least one selected from GSK-3 inhibitor XVI (CAS 252917-06-9), (2'Z,3'E)-6-bromoindirubin-3'-oxime (CAS 667463-62-9), 1H-pyrazolo[3,4-b]quinoxalin-3-amine (CAS 40254-90-8), (2,4-dichlorophenyl)-4-(1-methyl-1H-indol-3-yl)-1H-pyrrol-2,5-dione (CAS 280744-09-4), 3-[(3-chloro-4-hydroxyphenyl)amino]-4-(2-nitrophenyl)-1H-pyrrol-2,5-dione (CAS 264218-23-7), and GSK-3β inhibitor XII (CAS 601514-19-6) is preferred, and GSK-3 inhibitor XVI is more preferred.

The above-mentioned Wnt signaling agonists may be prepared by a usual method, or a commercial product may be used. The content of a Wnt signaling agonist in the differentiation medium can be suitably selected depending on the culture condition, the type of a Wnt signaling agonist to be used, and the like, in the range in which a Wnt signaling is activated, and cell proliferation is not arrested. For example, when GSK-3 inhibitor XVI is used as a Wnt signaling agonist, the concentration of the Wnt signaling agonist in the medium is preferably 0.5 μM or higher, more preferably 2 μM or higher, and preferably 5 μM or lower, more preferably 4 μM or lower. Alternatively, the concentration range of the Wnt signaling agonist in the medium is preferably from 0.5 to 5 μM, more preferably from 2 to 4 μM. Even more preferably, the concentration of the Wnt signaling agonist in the medium is 3 μM.

In contrast, the differentiation medium culture used to induce differentiation of pluripotent stem cells to NCS cells preferably contains a TGFβ signal inhibitor and/or a BMP signal inhibitor. Hence, induction of differentiation to NCS cells is promoted, resulting in improvement of the yield of target SKPs. Examples of the TGFβ signal inhibitor include 4-[4-(1,3-benzodioxol-5-yl)-5-(2-pyridinyl)-1H-imidazol-2-yl]-benzamide [e.g., trade name: SB431542 (CAS 301836-41-9)]. Examples of the BMP signal inhibitor include noggin and LDN193189 (CAS 1062368-24-4). These TGFβ signal inhibitors and BMP signal inhibitors may be prepared according to usual methods, or commercial products may be used. The content of the TGFβ signal inhibitor and the BMP signal inhibitor in the differentiation medium used for preparation of NCS cells can be suitably selected depending on the culture condition, the type of a pluripotent stem cell to be used, the type of an inhibitor, and the like. For example, the concentration of SB431542 in the medium is preferably 1 μM or higher, more preferably 5 μM or higher, and preferably 30 μM or lower, more preferably 20 μM, or the concentration range is preferably from 1 to 30 μM, more preferably from 5 to 20 μM. For example, the concentration of noggin in the medium is preferably 10 ng/mL or higher, more preferably 100 ng/mL or higher, and preferably 1000 ng/mL or lower, more preferably 700 ng/mL, or the concentration range is preferably from 10 to 1000 ng/mL, more preferably from 100 to 700 ng/mL.

The culture condition for inducing differentiation of pluripotent stem cells to NCS cells can be suitably selected depending on the type of cells to be used and the like. For example, when iPS cells are used as pluripotent stem cells, the duration of culture for induction of differentiation to NCS cells is preferably 1 to 20 days. The culture condition for induction of differentiation of NCS cells to SKPs can also be suitably selected. For example, cells can be efficiently differentiated to SKPs by culturing NCS cells in a differentiation induction medium containing a Wnt signaling agonist for preferably 3 to 5 days. In the present invention, either adhesion culture or suspension culture can be selected as a technique for culturing cells, and adhesion culture is preferably selected.

In a preferred embodiment, the above-described differentiated SKPs are subcultured once or more times. SKPs can be obtained as a highly pure cell group by performing subculture. The method for subculturing SKPs and the number of times of subculture can be suitably selected from usual subculture methods depending on the culture condition and the like. For example, to obtain cells in an adhesion culture system, subculture is performed using a diluted culture after cells are exfoliated with enzymes or the like. To obtain cells in a suspension culture system, subculture is performed using a dilution culture.

Cells differentiated to NCS cells or SKPs can be identified on the basis of expressions of the above-described marker protein or marker gene for each cell. Alternatively, differentiation of cells to NCS cells or SKPs can be confirmed on the basis of the cell morphology by microscopy or the like.

Since differentiation of NCS cells to SKPs occurs with high probability by the method for preparing SKPs of the present invention, isolation and recovery of SKPs from cultured cells are not necessarily required. However, SKPs may be isolated and recovered from the culture to increase purity of SKPs. SKPs can be isolated and recovered by a usual method, for example, a method using a cell sorter or a method using magnetic beads.

As described above, in the present invention, the laminin and/or a fragment thereof are used as a culture scaffolding material for culture for induction of differentiation of pluripotent stem cells to NCS cells and for culture for induction of differentiation of NCS cells to SKPs. Therefore, in yet another embodiment, the present invention provides a scaffolding material for culture for induction of differentiation of NCS cells to SKPs, which contains the laminin and/or a fragment thereof as an active ingredient. Furthermore, the present invention provides a scaffolding material for culture for induction of differentiation of pluripotent stem cells to NCS cells, which contains the laminin and/or a fragment thereof as an active ingredient. In a preferred embodiment, the laminin and/or a fragment thereof contained in the scaffolding material for culture for induction of differentiation of pluripotent stem cells to NCS cells are the above-described perlecan-modified laminin or a fragment thereof.

In one embodiment, the scaffolding material of the present invention is provided in a form of a culture substrate containing the laminin and/or a fragment thereof, for example, a culture substrate (e.g., plate, mesh, dish) having a coating containing the laminin and/or a fragment thereof, more specifically a culture substrate to which the laminin and/or a fragment thereof are adsorbed by applying a coating agent containing the laminin and/or a fragment thereof; a coating agent containing the laminin and/or a fragment thereof; a culture medium containing the laminin and/or a fragment thereof, or the like. The culture substrate, a coating agent, and a culture medium which contain the laminin and/or a fragment thereof may contain a scaffolding material or a cell adhesion molecule other than the above-described the laminin and/or a fragment thereof. The coating agent may contain other components contained in a usual coating agent for a culture substrate (e.g., a buffer solution as a solvent). The culture medium may contain other components contained in a usual culture medium (e.g., a base medium, serum, a serum substitute, and a nutritional factor such as those described above). When the medium is used for culture for induction of differentiation of NCS cells to SKPs, the medium preferably contains the above-described Wnt signaling agonist, more preferably the Wnt signaling agonist, a serum substitute, EGF, and bFGF. When the medium is used for culture for induction of differentiation of pluripotent stem cells to NCS cells, the medium contains preferably the above-described TGFβ signal inhibitor and/or BMP signal inhibitor.

In one embodiment, the scaffolding material of the present invention may consist of the laminin and/or a fragment thereof. In this case, the scaffolding material of the present invention is preferably added to a coating agent of a culture substrate or added to a medium for use.

When the scaffolding material of the present invention is a culture substrate containing the laminin and/or a fragment thereof, the content of the laminin and/or a fragment thereof in the culture substrate can be preferably from 0.05 to 50 μg, more preferably from 0.1 to 10 μg per $cm^2$ of an area of the culture substrate brought into contact with a culture. When the scaffolding material of the present invention is a coating agent containing the laminin and/or a fragment thereof, the content of the laminin and/or a fragment thereof in the coating agent can be preferably from 0.05 to 50 μg, more preferably from 0.1 to 10 μg per $cm^2$ of an area coated with the coating agent. When the scaffolding material of the present invention is a medium containing the laminin and/or a fragment thereof, the content of the laminin and/or a fragment thereof in the medium can be preferably from 0.1 to 100 μg, more preferably from 0.2 to 20 μg per mL of the medium at a final concentration. When the scaffolding material of the present invention is added to a coating agent of a culture substrate for use, the amount used can be adjusted to the above-described range so that the content of the laminin and/or a fragment thereof in the coating agent should fall in the above-described range. Alternatively, when the scaffolding material of the present invention is added to a medium for use, the amount used can be adjusted to the above-described range so that the final concentration of the laminin and/or fragment thereof per mL of the medium should fall in the above-described range.

In yet another embodiment, the present invention provides a culture substrate for culture for induction of differentiation of NCS cells to SKPs containing the scaffolding material of the present invention. Additionally, the present invention provides a cell culture kit for culture for induction of differentiation of NCS cells to SKPs containing the scaffolding material of the present invention.

In yet another embodiment, the present invention provides a culture substrate for culture for induction of differentiation of pluripotent stem cells to NCS cells containing the scaffolding material of the present invention. Additionally, the present invention provides a cell culture kit for culture for induction of differentiation of pluripotent stem cells to NCS cells containing the scaffolding material of the present invention. In a preferred embodiment, laminin and/or a fragment thereof contained in the scaffolding material of the present invention in the culture substrate or cell culture kit for culture for induction of differentiation of pluripotent stem cells to NCS cells are the above-described perlecan-modified laminin or a fragment thereof.

In a preferred embodiment, the culture substrate of the present invention is a culture substrate (e.g., plate, mesh, dish) having a coating containing the laminin and/or a fragment thereof, more preferably a culture substrate to which the laminin and/or a fragment thereof are adsorbed by applying a coating agent containing the laminin and/or a fragment thereof. In a preferred embodiment, the cell culture kit of the present invention may include, as necessary, a culture substrate, a differentiation medium for induction of differentiation of pluripotent stem cells to NCS cells or for induction of differentiation of NCS cells to SKPs and an additive thereof, a medium for maintenance culture of pluripotent stem cells and an additive thereof, and the like in addition to the laminin and/or a fragment thereof. The laminin and/or a fragment thereof contained in the cell culture kit of the present invention may be applied on a culture substrate or may be contained in a coating agent for coating a culture substrate or a medium.

The present invention also encompasses the following substances, manufacturing methods, purposes, methods, and so forth as exemplary embodiments. However, the present invention is not limited to these embodiments.

[1] A method for preparing a skin-derived pluripotent precursor cell, comprising culturing neural crest stem cells in the presence of at least one selected from the group consisting of laminin and a fragment thereof to differentiate the cells to skin-derived pluripotent precursor cells, wherein the laminin is at least one selected from the group consisting of laminin 111, laminin 121, laminin 332, laminin 421, laminin 511, laminin 521, and a variant thereof.

[2] The method according to [1], preferably further comprising a step of preparing the neural crest stem cells, the step comprising culturing pluripotent stem cells in the presence of at least one selected from the group consisting of laminin and a fragment thereof to differentiate the cells to neural crest stem cells, wherein the laminin is at least one selected from the group consisting of laminin 111, laminin 121, laminin 332, laminin 421, laminin 511, laminin 521, and a variant thereof.

[3] The method according to [2], preferably further comprising performing maintenance culture of the pluripotent stem cells previously in the presence of at least one selected from the group consisting of the laminin and the fragment thereof.

[4] The method according to any one of [1] to [3], wherein the laminin fragment is preferably a laminin fragment having an integrin binding activity, more preferably a laminin fragment comprising a laminin E8 fragment.

[5] The method according to any one of [1] to [4], wherein the at least one selected from the group consisting of the laminin and the fragment thereof preferably comprises the laminin or the fragment thereof bound to perlecan or a fragment comprising a growth factor binding site thereof, more preferably is the laminin or the fragment thereof bound to perlecan or a fragment comprising a growth factor binding site thereof.

[6] The method according to [5], wherein the perlecan or the fragment comprising a growth factor binding site thereof is preferably a fragment comprising any one of perlecan domains I to III, more preferably a fragment comprising perlecan domain I.

[7] The method according to any one of [1] to [6], wherein the culturing the neural crest stem cells in the presence of the at least one selected from the group consisting of the laminin and the fragment thereof preferably comprises culturing the cells on a culture substrate comprising the at least one selected from the group consisting of the laminin and the fragment thereof or culturing the cells in a medium comprising the at least one selected from the group consisting of the laminin and the fragment thereof.

[8] The method according to any one of [2] to [7], wherein the culturing the pluripotent stem cells in the presence of the at least one selected from the group consisting of the laminin and the fragment thereof preferably comprises culturing the cells on a culture substrate comprising the at least one selected from the group consisting of the laminin and the fragment thereof or culturing the cells in a medium comprising the at least one selected from the group consisting of the laminin and the fragment thereof.

[9] The method according to [7] or [8], wherein the amount of the at least one selected from the group consisting of the laminin and the fragment thereof to be used is preferably from 0.05 to 50 μg, more preferably from 0.1 to 10 μg per $cm^2$ of an area of the culture substrate brought into contact with a culture or preferably from 0.1 to 100 μg, more preferably from 0.2 to 20 μg as a final concentration per mL of the medium, or when the at least one selected from the group consisting of the laminin and the fragment thereof is added to a coating agent of the culture substrate for use, the content of the at least one selected from the group consisting of the laminin and the fragment thereof in the coating agent is preferably from 0.05 to 50 μg, more preferably from 0.1 to 10 μg per $cm^2$ of an area to be applied.

[10] The method according to any one of [1] to [9], wherein the culturing the neural crest stem cells preferably comprises culturing the cells in a differentiation medium comprising a Wnt signaling agonist.

[11] The method according to [10], wherein the Wnt signaling agonist is preferably a factor activating a β-catenin pathway, more preferably a β-catenin kinase inhibitor, even more preferably a GSK-3 inhibitor, even more preferably at least one selected from the group consisting of an aminopyrimidine compound, a bis-indole (indirubin) compound (BIO) or an acetoxime compound thereof, a thiadiazolidine (TDZD) compound, an oxothiadiazolidine-3-thione compound, a thienyl α-chloromethyl ketone compound, a phenyl α bromomethyl ketone compound, a thiazole-containing urea compound, 1H-pyrazolo[3,4-b]quinoxalin-3-amine, (2,4-dichlorophenyl)-4-(1-methyl-1H-indol-3-yl)-1H-pyrrol-2,5-dione, 3-[(3-chloro-4-hydroxyphenyl)amino]-4-(2-nitrophenyl)-1H-pyrrol-2,5-dione, a GSK-3β inhibitor XII, and a GSK-3β peptide inhibitor, even more preferably at least one selected from the group consisting of a GSK-3 inhibitor XVI, (2'Z,3'E)-6-bromoindirubin-3'-oxime (CAS 667463-62-9), 1H-pyrazolo[3,4-b]quinoxalin-3-amine, (2,4-dichlorophenyl)-4-(1-methyl-1H-indol-3-yl)-1H-pyrrol-2,5-dione, 3-[(3-chloro-4-hydroxyphenyl)amino]-4-(2-nitrophenyl)-1H-pyrrol-2,5-dione, and a GSK-3β inhibitor XII, even more preferably a GSK-3 inhibitor XVI.

[12] The method according to [10] or [11], wherein the concentration of the Wnt signaling agonist in the differentiation medium is preferably from 0.5 to 5 μM, more preferably from 2 to 4 μM.

[13] The method according to any one of [1] to [12], wherein the culturing the neural crest stem cells preferably comprises culturing the cells in a differentiation medium comprising a nutritional factor, wherein the nutritional factor is preferably at least one selected from the group consisting of a serum substitute, EGF, and bFGF, more preferably a serum substitute, EGF, and bFGF.

[14] The method according to [13], wherein the concentration of the serum substitute in the differentiation medium is preferably from 0.5 to 20 mass %, more preferably from 1 to 5 mass %, and the concentrations of the EGF and bFGF in the differentiation medium are preferably both from 1 to 100 ng/mL, more preferably from 10 to 50 ng/mL.

[15] The method according to any one of [2] to [14], wherein the step of culturing the pluripotent stem cells to differentiate the cell preferably comprises culturing the cells in a differentiation medium comprising at least one selected from the group consisting of a TGFβ signal inhibitor and a BMP signal inhibitor.

[16] The method according to [15], wherein the TGFβ signal inhibitor is preferably 4-[4-(1,3-benzodioxol-5-yl)-5-(2-pyridinyl)-1H-imidazol-2-yl]-benzamide, and the BMP signal inhibitor is noggin.

[17] The method according to any one of [1] to [16], wherein the skin-derived pluripotent precursor cells preferably co-express nestin and fibronectin.

[18] The method according to any one of [1] to [17], wherein the neural crest stem cells are preferably human-derived neural crest stem cells.

[19] The method according to any one of [1] to [18], wherein the neural crest stem cells are preferably neural crest stem cells derived from pluripotent stem cells.

[20] The method according to any one of [1] to [19], wherein the neural crest stem cells are preferably cultured without using a feeder cell.

[21] The method according to any one of [1] to [20], wherein the neural crest stem cells are preferably cultured in the absence of a xenogeneic component.

[22] A method for preparing neural crest stem cells, comprising culturing pluripotent stem cells in the presence of at least one selected from the group consisting of laminin and a fragment thereof bound to perlecan or a fragment comprising a growth factor binding site thereof to differentiate the cells to neural crest stem cells, wherein the laminin is at least one selected from the group consisting of laminin 111, laminin 121, laminin 332, laminin 421, laminin 511, laminin 521, and a variant thereof.

[23] The method according to [22], preferably further comprising performing maintenance culture of the pluripotent stem cells previously in the presence of the at least one selected from the group consisting of the laminin and the fragment thereof bound to perlecan or a fragment comprising a growth factor binding site thereof.

[24] The method according to [22] or [23], wherein the laminin fragment is preferably a laminin fragment having an integrin binding activity, more preferably a laminin fragment comprising laminin E8 fragment.

[25] The method according to any one of [22] to [24], wherein the perlecan or the fragment comprising a growth factor binding site thereof is preferably a fragment comprising any of perlecan domains I to III, more preferably a fragment comprising perlecan domain I.

[26] The method according to any one of [22] to [25], wherein the culturing the cells in the presence of the at least one selected from the group consisting of the laminin and the fragment thereof bound to perlecan or a fragment comprising a growth factor binding site thereof preferably comprises culturing the cells on a culture substrate comprising the at least one selected from the group consisting of the laminin and the fragment thereof bound to perlecan or a fragment comprising a growth factor binding site thereof or culturing the cells in a medium comprising the at least one selected from the group consisting of the laminin and the fragment thereof bound to perlecan or a fragment comprising a growth factor binding site thereof.

[27] The method according to [26], wherein the amount of the at least one selected from the group consisting of the laminin and the fragment thereof bound to perlecan or a fragment comprising a growth factor binding site thereof to be used is preferably from 0.05 to 50 μg, more preferably from 0.1 to 10 μg per $cm^2$ of an area of the culture substrate brought into contact with a culture or preferably from 0.1 to 100 μg, more preferably from 0.2 to 20 μg as a final concentration per mL of the medium, or when the at least one selected from the group consisting of the laminin and the fragment thereof is added to a coating agent of the culture substrate and used, the content of the at least one selected from the group consisting of the laminin and the fragment thereof in the coating agent is preferably from 0.05 to 50 μg, more preferably from 0.1 to 10 μg per $cm^2$ of an area to be applied.

[28] The method according to any one of [22] to [27], wherein the step of culturing the pluripotent stem cells to differentiate the cells preferably comprises culturing the cells in a differentiation medium comprising at least one selected from the group consisting of a TGFβ signal inhibitor and a BMP signal inhibitor, more preferably the TGFβ signal inhibitor is 4-[4-(1,3-benzodioxol-5-yl)-5-(2-pyridinyl)-1H-imidazol-2-yl]-benzamide, and the BMP signal inhibitor is noggin.

[29] The method according to any one of [22] to [28], wherein the pluripotent stem cells are preferably human-derived pluripotent stem cells.

[30] The method according to any one of [22] to [29], wherein the pluripotent stem cells are preferably cultured without using a feeder cell.

[31] The method according to any one of [22] to [30], wherein the pluripotent stem cells are preferably cultured in the absence of a xenogeneic component.

[32] A scaffolding material for culture for induction of differentiation of neural crest stem cells to skin-derived pluripotent precursor cells comprising at least one selected from the group consisting of laminin and a fragment thereof as an active ingredient, wherein the laminin is at least one selected from the group consisting of laminin 111, laminin 121, laminin 332, laminin 421, laminin 511, laminin 521, and a variant thereof.

[33] A scaffolding material for culture for induction of differentiation of pluripotent stem cells to neural crest stem cells comprising at least one selected from the group consisting of laminin and a fragment thereof bound to perlecan or a fragment comprising a growth factor binding site thereof as an active ingredient, wherein the laminin is at least one selected from the group consisting of laminin 111, laminin 121, laminin 332, laminin 421, laminin 511, and laminin 521, and a variant thereof.

[34] The scaffolding material according to [32] or [33], wherein the laminin fragment is preferably a laminin fragment having an integrin binding activity, more preferably a laminin fragment comprising a laminin E8 fragment.

[35] The scaffolding material according to any one of [32] to [34], wherein the at least one selected from the group consisting of the laminin and the fragment thereof preferably comprises the laminin or the fragment thereof bound to perlecan or a fragment comprising a growth factor binding site thereof, more preferably is the laminin or the fragment thereof bound to perlecan or a fragment comprising a growth factor binding site thereof.

[36] The scaffolding material according to any one of [33] to [35], wherein the perlecan or the fragment comprising a growth factor binding site thereof is preferably a fragment comprising any of perlecan domains I to III, more preferably a fragment comprising perlecan domain I.

[37] The scaffolding material according to any one of [32] to [36], the scaffolding material preferably being a culture substrate comprising the at least one selected from the group consisting of the laminin and the fragment thereof, a culture substrate having a coating agent comprising the at least one selected from the group consisting of the laminin and the fragment thereof, a coating agent comprising the at least one selected from the group consisting of the laminin and the fragment thereof, or a medium comprising the at least one selected from the group consisting of the laminin and the fragment thereof.

[38] The scaffolding material according to [37], wherein the content of the at least one selected from the group consisting of the laminin and the fragment thereof in the culture substrate is preferably from 0.05 to 50 μg, more preferably from 0.1 to 10 μg per $cm^2$ of an area of the culture substrate brought into contact with a culture, the content of the at least one selected from the group consisting of the laminin and the fragment thereof in the medium is preferably from 0.1 to 100 μg, more preferably from 0.2 to 20 μg per mL of the medium as a final concentration, or the content of the at least one selected from the group consisting of the laminin and the fragment thereof in the coating agent is preferably from 0.05 to 50 μg, more preferably from 0.1 to 10 μg per $cm^2$ of an area to be applied with the coating agent.

[39] A culture substrate for culture for induction of differentiation of neural crest stem cells to skin-derived pluripotent precursor cells, comprising the scaffolding material according to any one of [32] and [34] to [38].

[40] A cell culture kit for culture for induction of differentiation of neural crest stem cells to skin-derived pluripotent precursor cells, comprising the scaffolding material according to any one of [32] and [34] to [38].

[41] A culture substrate for culture for induction of differentiation of pluripotent stem cells to neural crest stem cells, comprising the scaffolding material according to any one of [33] to [38].

[42] A cell culture kit for culture for induction of differentiation of pluripotent stem cells to neural crest stem cells, comprising the scaffolding material according to any one of [33] to [38].

[43] Use of at least one selected from the group consisting of laminin and a fragment thereof in manufacture of a scaffolding material for culture for induction of differentiation of neural crest stem cell to skin-derived pluripotent precursor cells, wherein the laminin is at least one selected from the group consisting of laminin 111, laminin 121, laminin 332, laminin 421, laminin 511, laminin 521, and a variant.

[44] Use of at least one selected from the group consisting of laminin and a fragment thereof bound to perlecan or a fragment comprising a growth factor binding site thereof in manufacture of a scaffolding material for culture for induction of differentiation of pluripotent stem cells to neural crest stem cells, wherein the laminin is at least one selected from the group consisting of laminin 111, laminin 121, laminin 332, laminin 421, laminin 511, laminin 521, and a variant thereof.

[45] Use of at least one selected from the group consisting of laminin and a fragment thereof as a scaffolding material for culture for induction of differentiation of neural crest stem cells to skin-derived pluripotent precursor cells, wherein the laminin is at least one selected from the group consisting of laminin 111, laminin 121, laminin 332, laminin 421, laminin 511, laminin 521, and a variant thereof.

[46] Use of at least one selected from the group consisting of laminin and a fragment thereof bound to perlecan or a fragment comprising a growth factor binding site thereof as a scaffolding material for culture for induction of differentiation of pluripotent stem cells to neural crest stem cells, wherein the laminin is at least one selected from the group consisting of laminin 111, laminin 121, laminin 332, laminin 421, laminin 511, laminin 521, and a variant thereof.

[47] The use according to any one of [43] to [46], wherein the laminin fragment is preferably a laminin fragment having an integrin binding activity, more preferably a laminin fragment comprising a laminin E8 fragment.

[48] The use according to any one of [43] to [47], wherein the at least one selected from the group consisting of the laminin and the fragment thereof preferably comprises the laminin or the fragment thereof bound to perlecan or a fragment comprising a growth factor binding site thereof, more preferably is the laminin or the fragment thereof bound to perlecan or a fragment comprising a growth factor binding site thereof.

[49] The use according to any one of [44] and [46] to [48], wherein the perlecan or the fragment comprising a growth factor binding site thereof is preferably a fragment comprising any of perlecan domains I to III, more preferably a fragment comprising perlecan domain I.

[50] The use according to any one of [43] to [49], wherein the scaffolding material is preferably a culture substrate comprising the at least one selected from the group consisting of the laminin and the fragment thereof, a culture substrate having a coating comprising the at least one selected from the group consisting of the laminin and the fragment thereof, a coating agent comprising the at least one selected from the group consisting of the laminin and the fragment thereof, or a medium comprising the at least one selected from the group consisting of the laminin and the fragment thereof.

[51] The use according to [50], wherein the content of the at least one selected from the group consisting of the laminin and the fragment thereof in the culture substrate is preferably from 0.05 to 50 μg, more preferably from 0.1 to 10 μg per $cm^2$ of an area of the culture substrate brought into contact with a culture, the content of the at least one selected from the group consisting of the laminin and the fragment thereof in the medium is preferably from 0.1 to 100 μg, more preferably from 0.2 to 20 μg per mL of the medium as a final concentration, or the content of the at least one selected from the group consisting of the laminin and the fragment thereof in the coating agent is preferably from 0.05 to 50 μg, more preferably from 0.1 to 10 μg per $cm^2$ of an area applied with the coating agent.

[52] At least one selected from the group consisting of laminin and a fragment thereof for use as a scaffolding material for culture for induction of differentiation of neural crest stem cells to skin-derived pluripotent precursor cells, wherein the laminin is at least one selected from the group consisting of laminin 111, laminin 121, laminin 332, laminin 421, laminin 511, laminin 521, and a variant thereof.

[53] At least one selected from the group consisting of laminin and a fragment thereof bound to perlecan or a fragment comprising a growth factor binding site thereof for use as a scaffolding material for culture for induction of differentiation of pluripotent stem cells to neural crest stem cells, wherein the laminin is at least one selected from the group consisting of laminin 111, laminin 121, laminin 332, laminin 421, laminin 511, laminin 521, and a variant thereof.

[54] The method according to any one of [1] to [31], the method being an ex vivo method.

[55] The method according to any one of [1] to [31], wherein the culture does not include culture on or in a living human or an animal body.

[56] The use according to any one of [43] to [51], the use being ex vivo use.

[57] The use according to any one of [43] to [51], the use not including use on or in a living human or an animal body.

EXAMPLES

The present invention is explained more specifically below through examples. However, the technical scope of the present invention is not limited to these examples.

Reference Example 1: Preparation of Laminin

As laminin fragments for scaffolding, a laminin 111 E8 fragment (LM111E8), a laminin 121 E8 fragment (LM121E8), a laminin 332 E8 fragment (LM332E8), a laminin 421 E8 fragment (LM421E8), a laminin 511 E8 fragment (LM511E8), and a laminin 521 E8 fragment (LM521E8) were prepared according to a method described in International Publication No. WO 2014/103534.

Reference Example 2: Preparation of Perlecan-Modified Laminin (1) Preparation of Perlecan-Modified LM511E8 (P-LM511E8)

A laminin 511 E8 fragment in which the domain I ($Gly^{25}$-$Pro^{196}$) of a human perlecan fragment (hereinafter also referred to as Pln-D1) was fused to the C-terminus of a human laminin α5 chain E8 fragment (hereinafter also referred to as perlecan-modified LM511E8 or P-LM511E8) was prepared by the following procedures according to a method described in International Publication No. WO 2014/199754.

(1-1) Preparation of Expression Vector for Human Laminin α5 Chain, β1 Chain, and γ1 Chain E8 Fragments First, PCR was performed using a cloning plasmid pBluescript KS(+) (Stratagene) as a template and the following three different primer sets to prepare three different plasmids pBluescript KS(+) having a DNA sequence coding for 6× His tag (HHHHHH), a DNA sequence coding for a HA (hemagglutinin) tag (YPYDVPDYA), or a DNA sequence coding for a FLAG tag (DYKDDDDK) inserted at the 5' end of the EcoRV in the multicloning site of the plasmid.

(i) Primers for Introduction of 6× His Tag

```
(forward, SEQ ID NO: 1)
5'-ATGATGATGAAGCTTATCGATACCGT-3'

(reverse, SEQ ID NO: 2)
5'-CATCATCATGATATCGAATTCCTGCA-3'
```

(ii) Primers for Introduction of HA Tag

```
(forward, SEQ ID NO: 3)
5'-ATCATATGGATAAAGCTTATCGATACCGT-3'

(reverse, SEQ ID NO: 4)
5'-GTGCCAGATTATGCAGATATCGAATTCCT-3'
```

(iii) Primers for Introduction of FLAG Tag

```
(forward, SEQ ID NO: 5)
5'-ATCCTTGTAATCAAGCTTATCGATACCGT-3'

(reverse, SEQ ID NO: 6)
5'-GATGATGATAAGGATATCGAATTCCT-3'
```

Subsequently, PCR was performed using a plasmid containing full-length nucleotide sequences of human laminin α5 chain, β1 chain, and γ1 chain (The Journal of Biological Chemistry, 2004, 279:10946-10954) as a template and the following primers to amplify the regions corresponding to an α5 chain E8 fragment ($Ala^{2534}$-$Ala^{3327}$), a β1 chain E8 fragment ($Leu^{1561}$-$Leu^{1786}$), and a γ1 chain E8 fragment ($AsN^{1362}$-$Pro^{1690}$)

(iv) Primers for Amplification of α5 Chain E8 Fragment

```
(forward, SEQ ID NO: 7)
5'-GCTGCCGAGGATGCTGCTGGCCAGG-3'
```

-continued

```
(reverse, SEQ ID NO: 8)
5'-CTAGGCAGGATGCCGGGCGGGCTGA-3'
```

(v) Primers for Amplification of β1 Chain E8 Fragment

```
(forward, SEQ ID NO: 9)
5'-CTTCAGCATAGTGCTGCTGACATTG-3'

(reverse, SEQ ID NO: 10)
5'-TTACAAGCATGTGCTATACACAGCAAC-3'
```

(vi) Primers for Amplification of γ1 Chain E8 Fragment

```
(forward, SEQ ID NO: 11)
5'-AATGACATTCTCAACAACCTGAAAG-3'

(reverse, SEQ ID NO: 12)
5'-CTAGGGCTTTTCAATGGACGGGGTG-3'
```

The amplified DNA fragments were inserted at the EcoRV site in the multicloning site of pBluescript KS(+) having a tag sequence added, then the amplified DNA fragment containing a sequence coding for the tag on the 5' end was excised with restriction enzymes EcoRI and HindIII, and the fragments were inserted into a mammalian cell expression vector pSecTag2B (Invitrogen, containing a DNA sequence coding for a mouse Ig-κ chain V-J2-C signal peptide therein) to prepare expression vectors of a human α5 chain E8 fragment (containing a 6× His tag on the N-terminal side), a human β1 chain E8 fragment (containing a HA tag on the N-terminal side), and a human γ1 chain E8 fragment (containing a Flag tag on the N-terminal side).

(1-2) Preparation of Expression Vector for Perlecan Domain-Fused Laminin α5 Chain E8 Fragment PCR was performed using an expression vector for a human laminin α5 chain E8 fragment as a template and the following primers to amplify a DNA fragment coding for a C-terminal portion ($Leu^{570}$-$Pro^{772}$) of a human laminin α5 chain E8 fragment and a linker sequence (DAEDSKLL-PEPRAFP, SEQ ID NO: 13) between the G3 and G4 domains of a human laminin α1 chain.

(vii) Primers for Amplification to Introduce Linker Sequence

5'-CCTCAAGCGGCTGAACACGACAGGCG-3' (forward, SEQ ID NO: 14)

5'-ATATGGATCCTG-GAAAAGCCCGGGGCTCTGGCAAGAGCTTGCTGTCCTCTGCATCAGGCCCCAGGCCCGG-3' (reverse, SEQ ID NO: 15, containing a recognition sequence of a restriction enzyme BamHI)

The obtained DNA fragment was digested with restriction enzymes AscI (this recognition sequence of the restriction enzyme exists in a DNA sequence coding for the C-terminal portion of the human laminin α5 chain E8 fragment) and BamHI to obtain DNA fragment 1.

PCR was performed using a human perlecan expression vector (Journal of Biological Chemistry, 2010, 285(47): 36645-36655) as a template and the following primers to amplify a DNA fragment coding for a sequence of domain I of human perlecan (Pln-D1) ($Gly^{25}$-$Pro^{196}$) having a His tag added to the C-terminus.

(viii) Primers for Amplification of Pln-D1 Sequence

5'-ATATATATGGATCCGGGCTGAGGGCATAC-GATGGCTTGTCTCTG-3' (forward, SEQ ID NO: 16, containing a recognition sequence of a restriction enzyme BamHI)

5'-ATATATATGCGGCCGCCTAATGATGATGATGAT-GATGTGGGAACTGGGGCACTGTGCCCAG-3' (reverse, SEQ ID NO: 17, containing a recognition sequence of a restriction enzyme NotI)

The obtained DNA fragment was digested with restriction enzymes BamHI and NotI and designated as DNA fragment 2.

The above-described DNA fragments 1 and 2 were inserted into an expression vector fragment containing an N-terminal portion ($Met^1$-$Asp^{610}$) of a human laminin α5 chain E8 fragment obtained by digesting an expression vector for the human laminin α5 chain E8 fragment with restriction enzymes AscI and NotI to prepare an expression vector for a Pln-D1 fused human laminin α5 chain E8 fragment.

(1-3) Expression and Purification of Pln-D1-Fused Laminin Fragment

The expression vector for a Pln-D1-fused human laminin α5 chain E8 fragment was mixed with an expression vector for a human β1 chain E8 fragment (containing HA tag on the N-terminal side) and an expression vector for a human γ1 chain E8 fragment (containing Flag tag on the N-terminal side), the mixture was transfected into human kidney-derived 293F cells, and the cells were cultured for 72 hours. Then, a cultured broth was collected, and a Pln-D1-fused laminin 511 E8 fragment (P-LM511E8) was purified by affinity chromatography using Ni-NTA agarose and ANTI-FLAG M2 affinity gel (Sigma).

(2) Preparation of Perlecan-Modified LM111E8 (P-LM111E8)

A Pln-D1-fused laminin 111 E8 fragment (P-LM111E8) was prepared by the same procedure as in (1), except that α5 chain E8 was changed to α1 chain E8.

(3) Preparation of Perlecan-Modified LM121E8 (P-LM121E8)

A Pln-D1-fused laminin 121 E8 fragment (P-LM121E8) was prepared by the same procedure as in (1), except that α5 chain E8 was changed to α1 chain E8, and β1 chain E8 was changed to β2 chain E8.

(4) Preparation of Perlecan-Modified LM332E8 (P-LM332E8)

A Pln-D1-fused laminin 332 E8 fragment (P-LM332E8) was prepared by the same procedure as in (1), except that an α3 chain, a β3 chain, and a γ2 chain were used as an α chain, a β chain, and a γ chain.

(5) Preparation of Perlecan-Modified LM421E8 (P-LM421E8)

A Pln-D1-fused laminin 421 E8 fragment (P-LM421E8) was prepared by the same procedure as in (1), except that an α4 chain, a β2 chain, and a γ1 chain were used as an α chain, a β chain, and a γ chain.

(6) Preparation of Perlecan-Modified LM521E8 (P-LM521E8)

A Pln-D1-fused laminin 521 E8 fragment (P-LM521E8) was prepared by the same procedure as in (1), except that β1 chain E8 was changed to β2 chain E8.

Example 1: Construction of Laminin Scaffolding (1) Construction of Laminin Scaffolding Various laminins prepared in Reference Example 1 or perlecan-modified laminin prepared in Reference Example 2 were used to coat a culture substrate previously or added to a medium together with cells. In case of coating the culture substrate previously, each of various laminins was dissolved in Dulbecco's phosphate-buffered saline (DPBS) (Life Technologies, Catalog Number: 14190-250), and the obtained laminin solution (containing 2.5 μg/mL laminins) was spread on the surface of a culture substrate (35-mm dish) (the final concentration of laminin: approximately 0.5 $\mu g/cm^2$ of a coated area), allowed to stand at 37° C. for one hour, and washed with DPBS to form a coating on the culture substrate. In case of adding laminin to the medium, the amount of each of various laminins added to the medium was adjusted to have a final concentration range of 1.25 μg/mL in the medium. Cell culture was performed in the culture environment containing these laminin scaffoldings in the following examples.

Example 2: Preparation of Skin-Derived Pluripotent Precursor Cells (SKPs)

(1) Culture of iPS Cells

Human-derived iPS cells (clone name: 1231A3, purchased from Center for iPS Cell Research and Application, Kyoto University [CiRA]) were used as pluripotent stem cells. Of note, the strain 1231A3 is iPS cells obtained by introducing pCE-hOCT3/4, pCE-hSK, pCE-hUL, pCE-mp53DD, and pCXB-EBNA1 into peripheral blood mononuclear cells of a female African American using an episomal vector. Maintenance culture of iPS cells was performed according to a culture method recommended by the acquisition organization. Specifically, cells were cultured at 37° C. in a 5% $CO_2$ incubator using StemFit (registered trade name) (AK02N, Ajinomoto Co., Inc.) as a medium for human iPS cells according to a method described in Sci. Rep, 4, 2014, 3594; DOI:10.1038/srep03594. LM111E8, LM121E8, LM332E8, LM421E8, LM511E8, and LM521E8 (all used to coat a dish previously by the procedure described in Example 1) were used as laminin fragments for scaffolding.

(2) Preparation of Human iPS Cell-Derived Neural Crest Stem (NCS) Cells

The iPS cells cultured in (1) were differentiated to NCS cells according to a method described in Nature Protocols, 2010, 5:688-701, or Cell Reports, 2013, 3:1140-1152. Differentiation to NCS cells was induced by culturing the iPS cells in StemFit (registered trade name) AK02N (no additive C added) medium containing noggin (R&D Systems, Catalog Number: 6057-NG-100/CF, 500 ng/mL) and/or SB431542 (Tocris Bioscience, Catalog Number: 1614, 10 μM) for five days to two weeks. Of note, laminin fragments used for coating at the time of culture of iPS cells remained as they were because they were not subcultured as scaffoldings in the culture for induction of differentiation at the time of induction of differentiation of iPS cells to NCS cells.

(3) Induction of Differentiation of NCS Cells to SKPs

The NCS cells prepared in (2) were cultured for three to five days in DMEM/F12 medium (Life Technologies, Catalog Number: 10565-018) containing B-27 (brand name) supplement (Life Technologies, Catalog Number: 17504-044, 2 mass %), EGF (R&D Systems, Catalog Number: 336-EG-200, 20 ng/mL), bFGF (Wako, Catalog Number: 064-04541, 40 ng/mL), penicillin/streptomycin (Life Technologies, Catalog Number: 15140-122, 50 U, 50 μg/mL), and CHIR99021 (Cayman Chemical, Catalog Number: 13122, 3 μM) to induce differentiation of NCS cells to SKPs. Of note, laminin fragments used for coating at the time of culture of iPS cells remained as they were because they were not subcultured as scaffoldings in a culture for induction of differentiation at the time of induction of differentiation of NCS cells to SKPs. Subsequently, the cells differentiated to SKPs were subcultured using a solution for isolating/dispersing cultured cells (trade name: Accutase, BD Biosciences, Catalog Number: 561527) without laminin fragment scaffoldings, and then the cells were further cultured in DMEM/F12 medium containing B-27 (brand name) supplement (2 mass %), EGF (20 ng/mL), bFGF (40 ng/mL), and penicillin/streptomycin (Life Technologies, Catalog Number: 15140-122, 50 U, 50 μg/mL).

(4) Expression of Marker Proteins

Expressions of marker proteins in the cells which were induced to differentiate in (3) were investigated. For the subcultured cells (iPS-SKPs P1) which were induced to differentiate in the presence of laminin, expressions of marker proteins specific to SKPs (nestin and fibronectin) were investigated by immunohistochemical fluorescence staining. The cells were washed with D-PBS(−) and immobilized with 4% paraformaldehyde for 15 minutes. The immobilized cells were washed with D-PBS(−), treated with a PBS solution containing Triton X-100 (0.5 mass %) for five minutes, washed with D-PBS(−) again, and blocked with 10% goat serum (Nichirei Corporation, Catalog Number: 426041) at room temperature for one hour. Subsequently, the cells were treated with primary antibodies (at room temperature for two hours) and secondary antibodies (at room temperature for one hour) listed in Table 2, the nucleus was stained with Hoechst 33258 (Dojindo Laboratories, Catalog Number: H341), then the cells were embedded in Fluoromount G (Southern Biotech, Catalog Number: 0100-01), and expressions of the marker proteins were observed under a fluorescence microscope.

TABLE 2

| | |
|---|---|
| Primary antibodies | Anti-nestin antibody (Millipore; MAB5326)<br>Anti-fibronectin antibody (Sigma Aldrich; F3648) |
| Secondary antibodies | Alexa Fluor 488 goat anti-mouse IgG (H + L) (Life Technologies; A11029)<br>Alexa Fluor 555 donkey anti-rabbit IgG (H + L) (Life Technologies; A31572) |

(5) Results

FIG. 1 shows microscopic photographs indicating induction of differentiation of NCS cells to SKPs. iPS-NCS (FIG. 1, first row) shows microscopic photographs of cells immediately before the initiation of differentiation induction, iPS-SKPs P0 (FIG. 1, second row) shows microscopic photographs of cells after four days of induction of differentiation (before subculture), and iPS-SKPs P1 (FIG. 1, third row) shows microscopic photographs of cells after subculture (all 40-fold magnifications). Expressions of the marker proteins (nestin and fibronectin) of SKPs in the obtained cells were observed under a fluorescence microscope. Of note, Hoechst staining performed at the same time revealed that viable cells existed at the positions where expressions of the markers were observed (FIG. 1, fourth row) (all 50-fold magnifications). As shown in FIG. 1, differentiation of NSCs to SKPs was observed in the culture environment containing laminin fragments 111, 121, 332, 421, 511, and 521. In particular, differentiation to SKPs was induced very efficiently in the presence of laminin fragments 111, 332, 421, and 511.

Example 3: Preparation of SKPs in the Presence of Modified Laminin Fragments (1) Preparation of SKPs NCS cells were prepared from iPS cells by the same procedure as in Example 2 (1) to (3), and differentiation of the obtained NCS cells to SKPs was induced. The concentration of CHIR99021 in a medium for inducing differentiation to SKPs was 3 μM. The duration of culture for induction of differentiation to SKPs was four days. LM111E8, LM121E8, LM332E8, LM421E8, LM511E8, and LM521E8 and perlecan-modified laminin fragments P-LM111E8, P-LM121E8, P-LM332E8, P-LM421E8, P-LM511E8, and P-LM521E8 (all used to coat the dish previously by the procedure described in Example 1) were used as laminin fragments for scaffolding to be used for maintenance culture of iPS cells, induction of differentiation to NCS cells, and induction of differentiation to SKPs. SKPs induced to differentiate were subcultured without a laminin fragment scaffolding. A total of nine days of culture was required to obtain SKPs from iPS cells.

Figure 2:
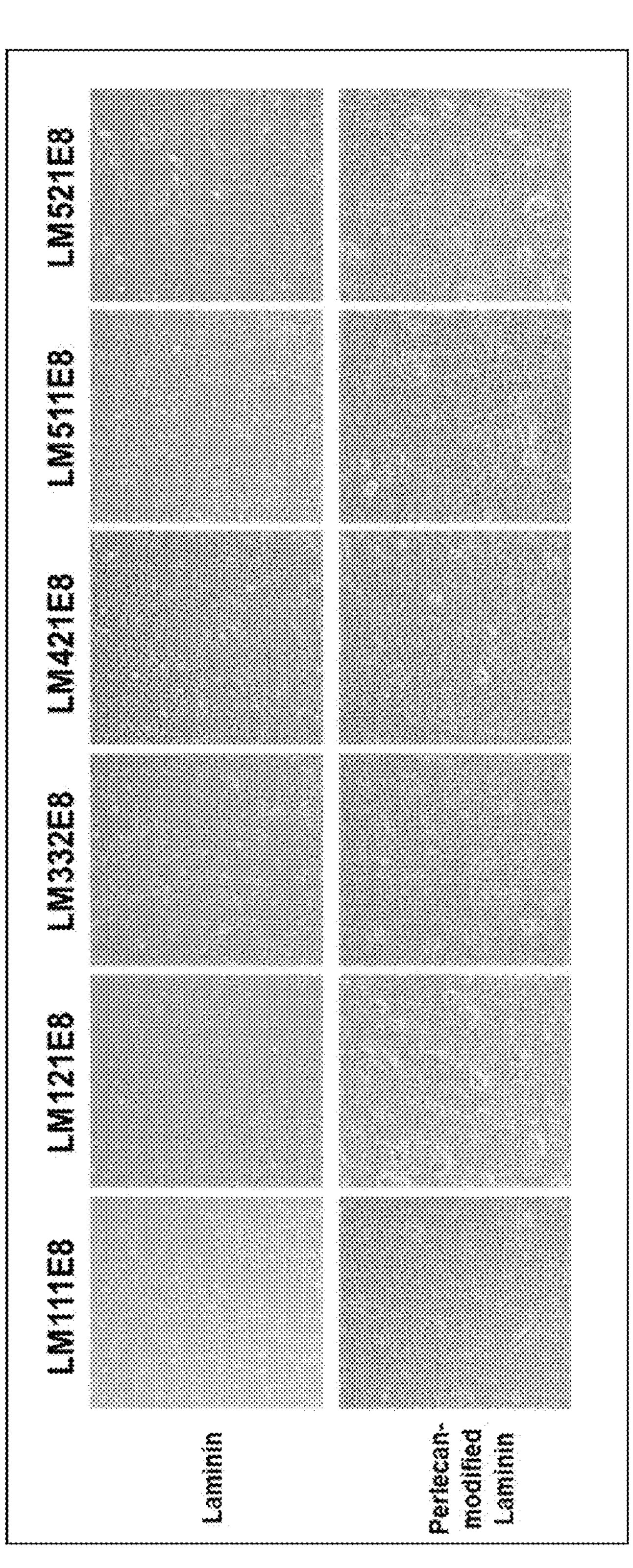
FIG. 2 shows induction of differentiation of iPS cells to SKPs in the presence of laminin fragments. The photographs show SKPs after subculture (all 40-fold magnifications). The upper row shows culture in the presence of unmodified laminin fragments; and the lower row shows culture in the presence of perlecan-modified laminin fragments.

FIG. 2 shows microscopic photographs of SKPs obtained by the procedure in (1). As shown FIG. 2, the efficiency in induction of differentiation of NSC cells to SKPs was increased in the presence of perlecan-modified laminin fragments, as compared with culture in the presence of unmodified laminin fragments.

(2) Expressions of Marker Genes

Expressions of marker genes in the cells which were induced to differentiate in (1) were investigated. The cells which were induced to differentiate in the presence of a perlecan-modified laminin fragment (P-LM111E8) were investigated by PCR for expressions of the marker genes listed in Table 3 after induction of differentiation and before subculture (iPS-SKPs P0) as well as after subculture (iPS-SKPs P1). Of the markers listed in Table 3, Nestin gene, Slug gene, Sox9 gene, Dermo-1 gene, BMP-4 gene, and Wnt-5a gene are markers of SKPs (Nat Cell Biol, 2004, 6:1082-1093, Stem Cell, 2005, 23:727-737), and Versican gene and CD133 gene are markers of hair papilla cells (J Dermatol Sci, 39, 2005, 147-154). GAPDH gene was used as a control.

Total RNA was extracted from a cell sample using RNeasy Mini Kit (QIAGEN, Catalog Number: 74104). The concentration of the extracted total RNA was measured, and reverse transcription reaction was performed using a specific amount of total RNA and High Capacity RNA-to-cDNA Kit (Applied Biosystems, Catalog Number: 4387406). PCR was performed in a 50-μL system using 1 μL of the obtained cDNA sample as a template and the primer sets listed in Table 3. KOD-Plus-Ver.2 (TOYOBO, Catalog Number: KOD-211) was used as an enzyme. PCR was performed according to a reaction protocol of 94° C. for two minutes→(at 98° C. for 10 seconds; at 63° C. for 30 seconds; 68° C. for 30 seconds)×25 to 35 cycles. Electrophoresis of 5 μL of the reaction mixture was performed at 100 V using 1.5% agarose gel (Takara Bio Inc., Catalog Number: 50071)/TBE buffer (Kanto Kagaku, Catalog Number: 46510-78).

TABLE 3

| Marker gene | Sense Primer (5'-3') | Anti-Sense Primer (5'-3') |
|---|---|---|
| GAPDH | CGGAGTCAACGGATTAGCCTTCTCCATGGTGGTGAA TGGTCG (SEQ ID NO: 18) | (SEQ ID NO: 19) |
| Nestin | CAGCGTTGGAACAGAGCTGGCACAGGTGTCTCAAG GGTTG (SEQ ID NO: 20) | (SEQ ID NO: 21) |
| Slug | CATCTTTGGGGCGAGCCCGTGTGAGTTCTAATGTGTC TGAGTCC (SEQ ID NO: 22) | (SEQ ID NO: 23) |
| Sox9 | GTCAGCCAGGTGCTCACTTGTAATCCGGGTGGTCC AAAGG (SEQ ID NO: 24) | (SEQ ID NO: 25) |

TABLE 3-continued

| Marker gene | Sense Primer (5'-3') | Anti-Sense Primer (5'-3') |
|---|---|---|
| Dermo-1 | GCAAGAAGTCGAGCGGGC AAGATG (SEQ ID NO: 26) | AATGGCAGCATCATTCAG (SEQ ID NO: 27) |
| BMP-4 | TTCTGCAGATGTTTGAGA GGCTGC (SEQ ID NO: 28) | GCCGAAGCTCTGCAGAG (SEQ ID NO: 29) |
| Wnt-5a | GGATGGCTGGAAGTGACA CAATG (SEQ ID NO: 30) | CAAACTGGTCCACGATC (SEQ ID NO: 31) |
| Versican | ACGATGCCTACTTTGTAG CCACC (SEQ ID NO: 32) | TGAAACACAACCCCATCC (SEQ ID NO: 33) |
| CD133 | ATGGCCCTCGTACTCCAC GGCTC (SEQ ID NO: 34) | GCGGCTGTACCACATAG (SEQ ID NO: 35) |

Figure 3:
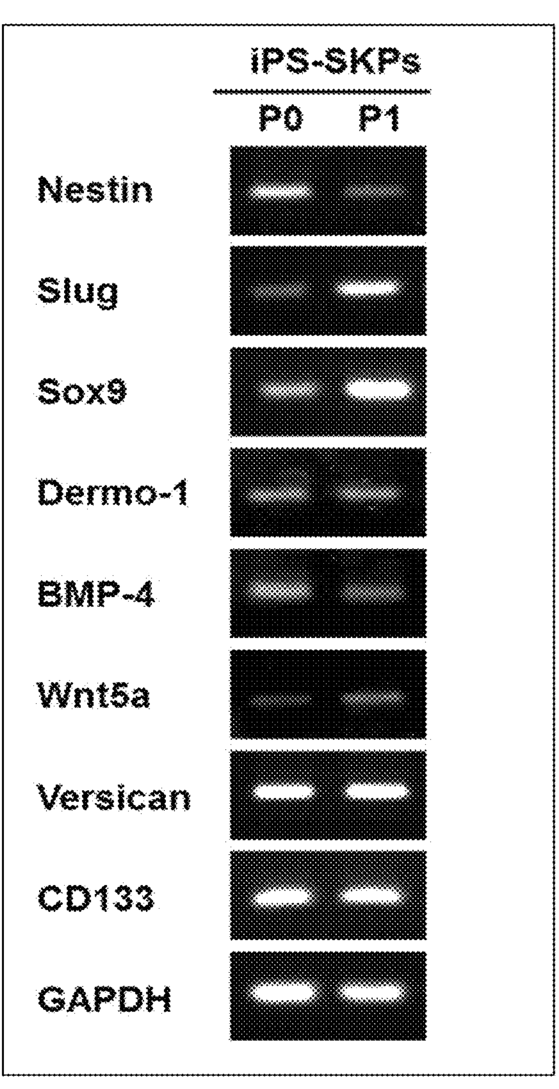
FIG. 3 shows expressions of marker genes in SKPs differentiated in the presence of perlecan-modified laminin fragments. iPS-SKPs P0 shows cells after induction of differentiation; and iPS-SKPs P1 shows cells after subculture.

FIG. 3 shows the results of electrophoresis. As shown in FIG. 3, expressions of the marker genes of SKPs were detected in the cells after induction of differentiation. Most of these markers of SKPs were expressed similarly in P0 and P1, or expressions were increased in P1. Therefore, it was confirmed that the cells which were induced to differentiate in (1) were SKPs.

(3) Expressions of Marker Proteins

Expressions of marker proteins in the cells which were induced to differentiate in (1) were investigated. The subcultured cells which were induced to differentiate in the presence of a perlecan-modified laminin fragment (P-LM111E8) (iPS-SKPs P1) were investigated for expressions of the marker proteins specific to SKPs (nestin, fibronectin, and αSMA) by immunohistochemical fluorescence staining following the same procedure as in Example 2 (4). The primary antibodies and the secondary antibodies used were as listed in Table 4.

TABLE 4

| | |
|---|---|
| Primary antibodies | Anti-nestin antibody (Millipore; MAB5326)<br>Anti-fibronectin antibody (Sigma Aldrich; F3648)<br>Anti-αSMA antibody (Sigma Aldrich; A2547) |
| Secondary antibodies | Alexa Fluor 488 goat anti-mouse IgG (H + L) (Life Technologies; A11029)<br>Alexa Fluor 555 donkey anti-rabbit IgG (H + L) (Life Technologies; A31572) |

Figure 4:
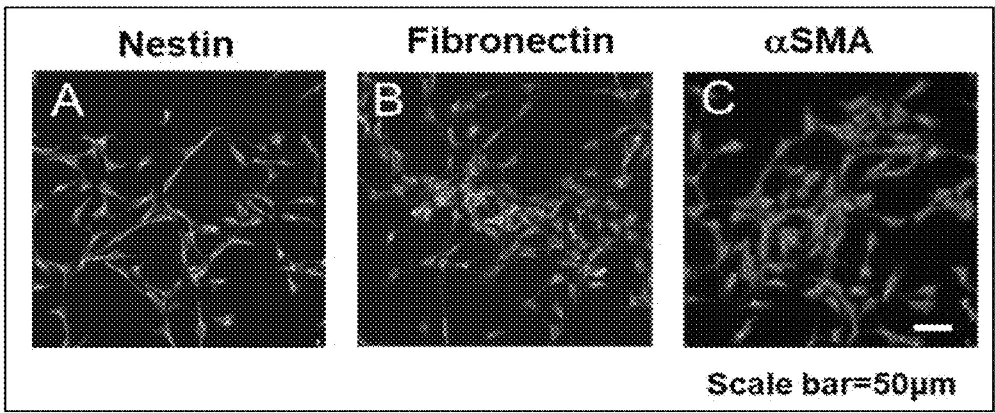
FIG. 4 shows expressions of marker proteins in SKPs differentiated in the presence of perlecan-modified laminin fragments. The photographs are fluorescence microscopic photographs of immunohistochemically stained cells. Panel A shows expression of nestin; Panel B shows expression of fibronectin; and Panel C shows expression of αSMA.

The results are shown in FIG. 4. Here, FIGS. 4(A), (B), and (C) are fluorescence microscopic photographs showing expressions of nestin, fibronectin, and αSMA, respectively. As shown in FIG. 4, expressions of the marker proteins specific to SKPs were observed in virtually all cells after subculture. Therefore, it was confirmed that the cells which were induced to differentiate in (1) were SKPs.

Example 4: Induction of Differentiation of SKPs to Tissue Cells

The subcultured SKPs which were induced to differentiate in the presence of a perlecan-modified laminin fragment (P-LM111E8) obtained in Example 3 were investigated for an ability to induce differentiation to tissue cells.

(1) Induction of Differentiation to Adipocytes

Subcultured SKPs ($3\times10^5$ cells) were seeded on a 35-mm dish. After 24 hours of culture, the medium was replaced with MEM medium (Life Technologies, Catalog Number: 42360-032) containing 3-isobutyl-1-methylxanthine (Sigma Aldrich, Catalog Number: I7018, 0.45 nM), insulin (Sigma Aldrich, Catalog Number: I3536, 2.07 μM), dexamethasone (Sigma Aldrich, Catalog Number: D4902, 100 nM), rabbit serum (Sigma Aldrich, Catalog Number: R4505, 15%), and penicillin/streptomycin (Life Technologies, Catalog Number: 15140-122, 100 U, 100 μg/mL), and cells were cultured for further two weeks. Subsequently, Oil Red O staining of the cells was performed using Oil Red O Staining Kit (ScienCell Research Laboratories, Inc., Catalog Number: 0843) according to the attached protocol.

(2) Induction of Differentiation to Bone Cells

Subcultured SKPs ($3\times10^5$ cells) were seeded on a 35-mm dish. After 24 hours of culture, the medium was replaced with MEM medium (Life Technologies, Catalog Number: 42360-032) containing dexamethasone (Sigma Aldrich, Catalog Number: D4902, 100 nM), β-glycerophosphate (Sigma Aldrich, Catalog Number: G9422, 10 mM), L-ascorbic acid-2-phosphate (Sigma Aldrich, Catalog Number: A8960, 50 μM), bovine serum (HyClone, Catalog Number: SH30070.03, 10 mass %), and penicillin/streptomycin (Life Technologies, Catalog Number: 15140-122, 100 U, 100 μg/mL), and the cells were cultured for further two weeks. Subsequently, the cells were stained with alkaline phosphatase using Alkaline Phosphatase Substrate Kit (Vector Laboratories, Catalog Number: SK-5300) according to the attached protocol.

(3) Induction of Differentiation to Schwann Cells

Using a medium for culture of SKPs [a DMEM/F12 medium (Life Technologies, Catalog Number: 10565-018) containing 2% B-27 (brand name) supplement (Life Technologies, Catalog Number: 17504-044), 20 ng/mL EGF (R&D Systems, Catalog Number: 336-EG-200), 40 ng/mL bFGF (Wako, Catalog Number: 064-04541), 50 U penicillin, and 50 μg/mL streptomycin (Life Technologies, Catalog Number: 15140-122], $4.8\times10^4$ subcultured SKP cells were seeded on a culture dish (35 mm dish) coated previously with 25-fold diluted laminin 111 (Sigma Aldrich, Catalog Number: L4544) and 0.1 mg/mL Poly-L-lysine (Sigma-Aldrich, Catalog Number: P4707). After 24 hours of culture, the medium was replaced with DMEM/F12 medium (Life Technologies, Catalog Number: 10565-018) containing 5 μM Forskolin (Sigma Aldrich, Catalog Number: F3917), 50 ng/mL heregulin-1β (PeproTech, Catalog Number: 100-03), 2% N2 supplement (Life Technologies, Catalog Number: 17502-048), and 1% bovine serum (HyClone, Catalog Number: SH30070.03E), and the cells were cultured for further two to three weeks. During the culture, the medium was replaced once every two to three days. The obtained cells were washed with D-PBS(−) and immobilized with 4% paraformaldehyde for 15 minutes. The immobilized cells were washed with D-PBS(−), treated with a PBS solution containing 0.5% Triton X-100 for five minutes, washed with D-PBS(−) again, and then blocked with 10% goat serum (Nichirei Corporation, Catalog Number: 426041) at room temperature for one hour. Subsequently, the cells were treated with primary antibodies (anti-S100β antibody, Sigma Aldrich, Catalog Number: S2532; at room temperature for two hours) and secondary antibodies (Alexa Fluor 488 goat anti-mouse IgG (H+L), Life Technologies, Catalog Number: A11029 at room temperature for one hour). Subsequently, the nucleus was stained with DAPI (Dojindo Laboratories, Catalog Number: FK045), then the cells were embedded in Fluoromount G (Southern Biotech, Catalog Number: 0100-

01), and expression of the marker protein specific to Schwann cells (S100β) was observed under a fluorescence microscope.

(4) Microscopic Observations

Figure 5:
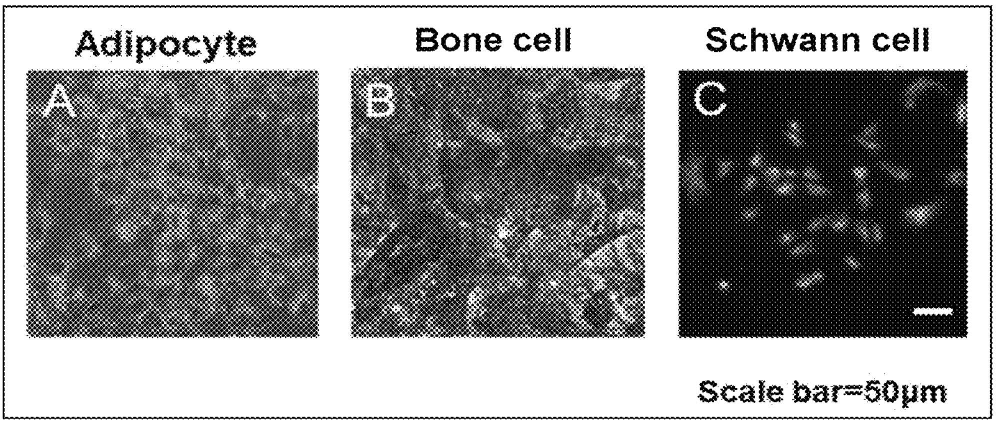
FIG. 5 shows differentiation of SKPs to tissue cells in the presence of perlecan-modified laminin fragments. The photographs are microscopic photographs of stained cells. Panel A shows adipocytes; Panel B shows bone cells; Panel C shows Schwann cells.

FIG. 5 shows microscopic images of the stained cells. In FIG. 5(A), stained lipids are observed in cells, indicating that SKPs were differentiated to adipocytes. In FIG. 5(B), alkaline phosphatase positive cells are observed, indicating that SKPs were differentiated to bone cells. In FIG. 5(C), S100β positive cells are observed, indicating that SKPs were differentiated to Schwann cells. Therefore, the cells obtained in Example 3 were shown to be SKPs capable of differentiation to adipocytes, bone cells, and glia cells such as Schwann cells.

Example 5: Preparation of SKPs Under Xeno-Free Condition

NCS cells were prepared from iPS cells under a xeno-free condition in the same procedure as in Example 2 (1) to (3), and then differentiation of the obtained NCS cells to SKPs was induced. As xeno-free reagents, noggin (SIGMA, Catalog Number: H66416-10UG, 500 ng/mL), B-27 (brand name) supplement Xenofree CTS (Life Technologies, Catalog Number: A14867-01, 2 mass %), EGF (Higeta Shoyu Co., Ltd., Catalog Number: REG100UG, 20 ng/mL), and bFGF (ReproCell Inc., Catalog Number: RCHEOT005,006, 40 ng/mL) were used. The concentration of CHIR99021 in a medium for inducing differentiation to SKPs was 3 μM. The duration of culture for induction of differentiation to SKPs was four days. LM111E8, LM511E8, and perlecan-modified laminin fragments P-LM111E8 and P-LM511E8 (all used to coat the dish previously by the procedure described in Example 1) were used as laminin fragments for scaffolding in maintenance culture of iPS cells, induction of differentiation to NCS cells, and induction of differentiation to SKPs.

Figure 6:
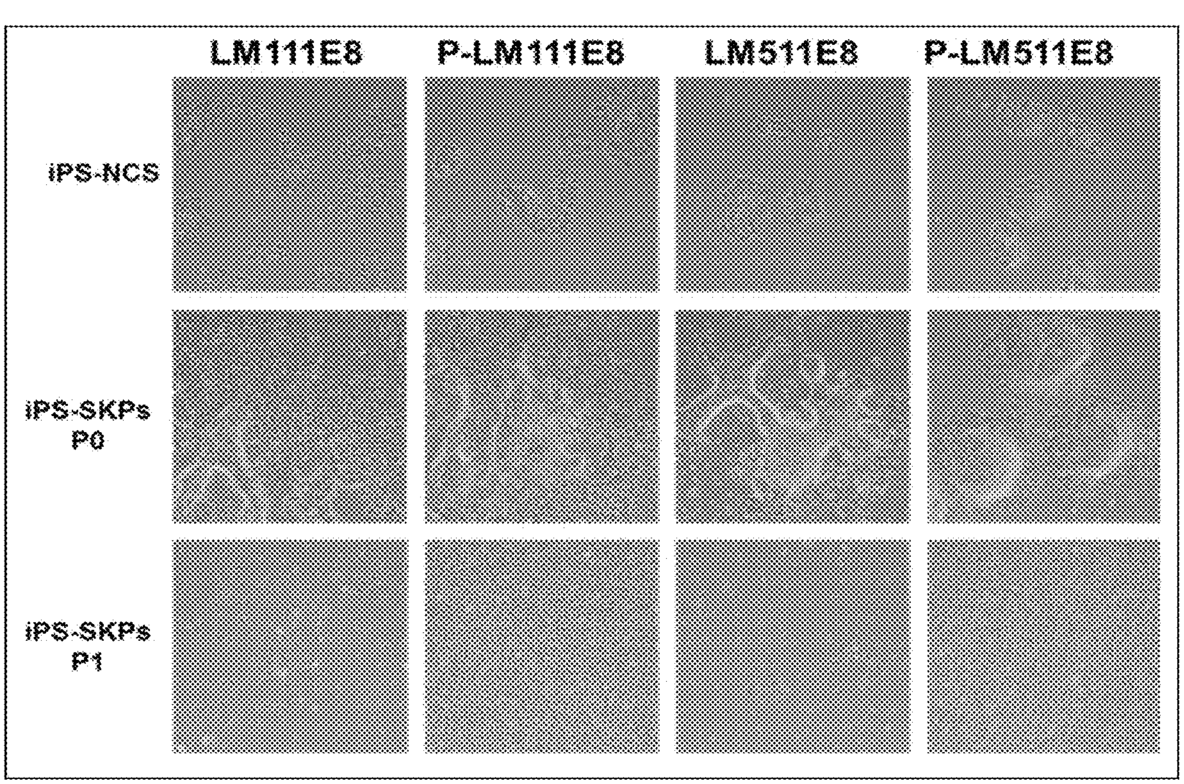
FIG. 6 shows induction of differentiation of iPS cells to SKPs in the presence of laminin fragments under a xeno-free condition. iPS-NCS (uppermost row) shows cells immediately before the initiation of induction of differentiation; iPS-SKPs P0 (middle row) shows cells after four days of induction of differentiation; iPS-SKPs P1 (lowermost row) shows cells after subculture (all 40-fold magnifications).

FIG. 6 shows microscopic photographs of induction of differentiation of the obtained NCS cells to SKPs. iPS-NCS (FIG. 6, uppermost row) shows microscopic photographs of cells immediately after the initiation of differentiation induction, iPS-SKPs P0 (FIG. 6, middle row) shows a microscopic photograph of cells after four days of induction of differentiation (before subculture), and iPS-SKPs P1 (FIG. 6 lowermost row) shows microscopic photographs of cells after subculture (all 40-fold magnifications). As shown in FIG. 6, differentiation to SKPs was enabled under a xeno-free condition in the presence of laminin fragments and perlecan-modified laminin fragments.

Example 6: Identification of Neural Crest Stem (NCS) Cells Derived from Human iPS Cells The properties of NCS cells which were induced to differentiate in the presence of a laminin fragment and a perlecan-modified laminin fragment (LM111E8 and P-LM111E8) obtained by the procedures of Example 2 (1) to (2) were investigated. Using the cells obtained from immediately before culture for differentiation to NCS cells by the procedure in Example 2 (2) (differentiation day 0, 0d) to 8 days of culture (8d), PCR was performed by the same procedure as in Example 3 (2) using 2 μL of cDNA sample as a template and primers and probes listed in Table 5 in a 20-μL system. PCR was performed using TaqMan Fast Universal PCR Master Mix (Applied Biosystems, Catalog Number: 4352042). Gene expression of a nerve growth factor receptor (p75) was detected as an indicator of differentiation to NCS cells. RPLP0 was used as an internal standard. Change in gene expression was indicated as a relative expression level based on the expression level normalized using the internal standard with the expression level of each gene at differentiation day 0 (0d) set to 1.

TABLE 5

| Name of gene | Primer |
|---|---|
| ribosomal protein lateral stalk subunit P0 (RPLP0) | Hs99999902_m1 |
| nerve growth factor receptor (p75) | Hs00609976_m1 |

Figure 7:
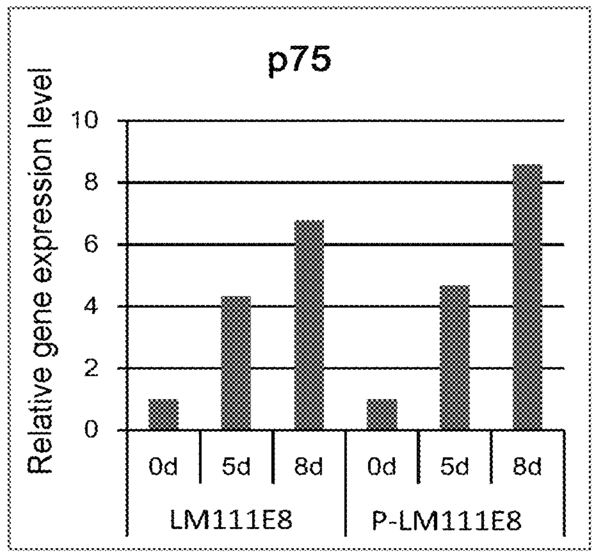
FIG. 7 shows expressions of a marker gene in NCS cells differentiated in the presence of laminin fragments.

The results are shown in FIG. 7. As the induction of differentiation proceeded, increased expression of p75, the marker gene of NCS cells, was observed. Therefore, it was found that differentiation to NCS cells could be induced on a laminin fragment and a modified laminin fragment.

Example 7: Percentage Differentiation Induction of SKPs in the Presence of Laminin Fragments Differentiation of SKPs was induced by the same procedure as in Example 3 (1). As laminin fragments for scaffolding, laminin fragments LM111E8, LM121E8, LM332E8, LM421E8, LM511E8, and LM521E8 and perlecan-modified laminin fragments P-LM111E8, P-LM121E8, P-LM332E8, P-LM421E8, P-LM511E8, and P-LM521E8 were used. The SKPs which were induced to differentiate (before subculture: iPS-SKPs P0) were subcultured at the same dilution rate in a 48-well plate (iPS-SKPs P1). Subculture was performed without a laminin fragment scaffolding. The number of cells in the culture after three days of subculture was counted using Cell Counting Kit-8 (Dojindo Laboratories, Catalog Number: 347-07621). The reagent solution of the kit was added to the culture, the cells were cultured for a specified time (one to three hours) in a 5% $CO_2$ incubator at 37° C., and then absorbance at 450 nm was measured using a microplate reader to assess the respiration activity (viable cell count) of the culture.

Figure 8:
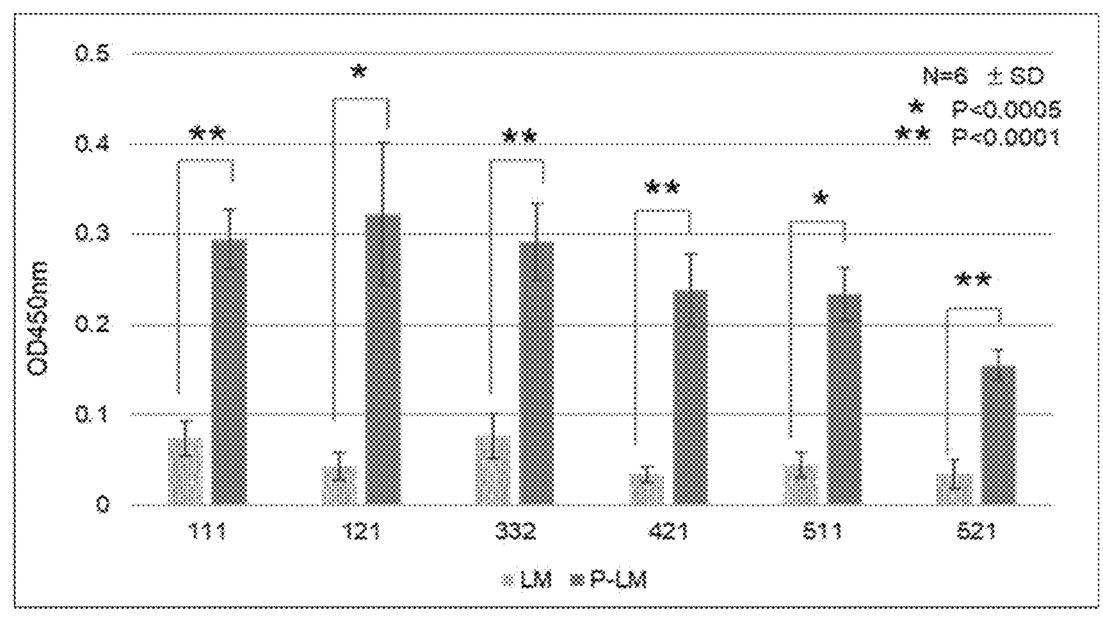
FIG. 8 shows the number of SKPs which were induced to differentiate in the presence of laminin fragments. LM denotes an unmodified laminin fragment; and P-LM denotes a perlecan-modified laminin fragment. The labels below each bar represent laminin types. Error bar=SD; *, $P<0.0005$; **:$P<0.0001$ (t test).

The results are shown in FIG. 8. Regardless of the type of a laminin fragment, differentiation was induced in significantly more cells when a perlecan-modified laminin fragment was used, as compared with an unmodified fragment (t test, $p<0.0005$).

The invention claimed is:

1. A method for preparing skin-derived pluripotent precursor cells, the method comprising:

culturing neural crest stem cells in the presence of a perlecan-modified laminin 111, a perlecan-modified laminin 121, a perlecan-modified laminin 332, a perlecan-modified laminin 421, a perlecan-modified laminin 511, a perlecan-modified laminin 521, or a combination thereof to differentiate the cells to skin-derived pluripotent precursor cells.

2. The method according to claim 1, further comprising preparing the neural crest stem cells, wherein the preparation comprises culturing pluripotent stem cells in the presence of the perlecan-modified laminin 111, the perlecan-modified laminin 121, the perlecan-modified laminin 332, the perlecan-modified laminin 421, the perlecan-modified laminin 511, the perlecan-modified laminin 521, or a combination thereof to differentiate the cells to neural crest stem cells.

3. The method according to claim 1, wherein the culturing the neural crest stem cells in the presence of the perlecan-modified laminin 111, the perlecan-modified laminin 121, the perlecan-modified laminin 332, the perlecan-modified laminin 421, the perlecan-modified laminin 511, the perlecan-modified laminin 521, or a combination thereof comprises culturing the cells on a culture substrate comprising the perlecan-modified laminin 111, the perlecan-modified laminin 121, the perlecan-modified laminin 332, the perlecan-modified laminin 421, the perlecan-modified laminin 511, the perlecan-modified laminin 521, or a combination thereof or culturing the cells in a medium comprising the perlecan-modified laminin 111, the perlecan-modified laminin 121, the perlecan-modified laminin 332, the perlecan-modified laminin 421, the perlecan-modified laminin 511, the perlecan-modified laminin 521, or a combination thereof.

4. The method according to claim 2, wherein the culturing the pluripotent stem cells in the presence of the perlecan-modified laminin 111, the perlecan-modified laminin 121, the perlecan-modified laminin 332, the perlecan-modified laminin 421, the perlecan-modified laminin 511, the perlecan-modified laminin 521, or a combination thereof comprises culturing the cells on a culture substrate comprising the perlecan-modified laminin 111, the perlecan-modified laminin 121, the perlecan-modified laminin 332, the perlecan-modified laminin 421, the perlecan-modified laminin 511, the perlecan-modified laminin 521, or a combination thereof or culturing the cells in a medium comprising the perlecan-modified laminin 111, the perlecan-modified laminin 121, the perlecan-modified laminin 332, the perlecan-modified laminin 421, the perlecan-modified laminin 511, the perlecan-modified laminin 521, or a combination thereof.

5. The method according to claim 1, wherein the culturing neural crest stem cells comprises culturing the cells in a differentiation medium comprising a Wnt signaling agonist.

6. The method according to claim 2, wherein the culturing pluripotent stem cells comprises culturing the cells in a differentiation medium comprising at least one selected from the group consisting of TGFβ signal inhibitor and BMP signal inhibitor.

7. The method according to claim 1, wherein the skin-derived pluripotent precursor cells co-expresses nestin and fibronectin.

8. The method according to claim 1, wherein the neural crest stem cells are human-derived neural crest stem cells.

9. The method according to claim 1, wherein the culturing the cells is performed without using feeder cells.

10. The method according to claim 1, wherein the culturing the cells is performed in the absence of a xenogeneic component.

* * * * *

SEQUENCE LISTING

```
<160> NUMBER OF SEQ ID NOS: 35

<210> SEQ ID NO 1
<211> LENGTH: 26
<212> TYPE: DNA
<213> ORGANISM: Artificial Sequence
<220> FEATURE:
```

<223> OTHER INFORMATION: Synthetic DNA Primer

<400> SEQUENCE: 1
atgatgatga agcttatcga taccgt 26

<210> SEQ ID NO 2
<211> LENGTH: 26
<212> TYPE: DNA
<213> ORGANISM: Artificial Sequence
<220> FEATURE:
<223> OTHER INFORMATION: Synthetic DNA Primer

<400> SEQUENCE: 2
catcatcatg atatcgaatt cctgca 26

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA Primer

<400> SEQUENCE: 3
atcatatgga taaagcttat cgataccgt 29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA Primer

<400> SEQUENCE: 4
gtgccagatt atgcagatat cgaattcct 29

<210> SEQ ID NO 5
<211> LENGTH: 29
<212> TYPE: DNA
<213> ORGANISM: Artificial Sequence
<220> FEATURE:
<223> OTHER INFORMATION: Synthetic DNA Primer

<400> SEQUENCE: 5
atccttgtaa tcaagcttat cgataccgt 29

<210> SEQ ID NO 6
<211> LENGTH: 26
<212> TYPE: DNA
<213> ORGANISM: Artificial Sequence
<220> FEATURE:
<223> OTHER INFORMATION: Synthetic DNA Primer

<400> SEQUENCE: 6
gatgatgata aggatatcga attcct 26

<210> SEQ ID NO 7
<211> LENGTH: 25
<212> TYPE: DNA
<213> ORGANISM: Artificial Sequence
<220> FEATURE:
<223> OTHER INFORMATION: Synthetic DNA Primer

<400> SEQUENCE: 7
gctgccgagg atgctgctgg ccagg 25

<210> SEQ ID NO 8
<211> LENGTH: 25
<212> TYPE: DNA
<213> ORGANISM: Artificial Sequence
<220> FEATURE:
<223> OTHER INFORMATION: Synthetic DNA Primer

<400> SEQUENCE: 8
ctaggcagga tgccgggcgg gctga 25

<210> SEQ ID NO 9
<211> LENGTH: 25
<212> TYPE: DNA
<213> ORGANISM: Artificial Sequence
<220> FEATURE:
<223> OTHER INFORMATION: Synthetic DNA Primer

<400> SEQUENCE: 9
cttcagcata gtgctgctga cattg 25

<210> SEQ ID NO 10
<211> LENGTH: 27
<212> TYPE: DNA
<213> ORGANISM: Artificial Sequence
<220> FEATURE:
<223> OTHER INFORMATION: Synthetic DNA Primer

<400> SEQUENCE: 10
ttacaagcat gtgctataca cagcaac 27

<210> SEQ ID NO 11
<211> LENGTH: 25
<212> TYPE: DNA
<213> ORGANISM: Artificial Sequence
<220> FEATURE:
<223> OTHER INFORMATION: Synthetic DNA Primer

<400> SEQUENCE: 11
aatgacattc tcaacaacct gaaag 25

<210> SEQ ID NO 12
<211> LENGTH: 25
<212> TYPE: DNA
<213> ORGANISM: Artificial Sequence
<220> FEATURE:
<223> OTHER INFORMATION: Synthetic DNA Primer

<400> SEQUENCE: 12
ctagggcttt tcaatggacg gggtg 25

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide linker peptide

<400> SEQUENCE: 13

```
Asp Ala Glu Asp Ser Lys Leu Leu Pro Glu Pro Arg Ala Phe Pro
1               5                   10                  15
```

<210> SEQ ID NO 14
<211> LENGTH: 26
<212> TYPE: DNA
<213> ORGANISM: Artificial Sequence
<220> FEATURE:
<223> OTHER INFORMATION: Synthetic DNA Primer

<400> SEQUENCE: 14
cctcaagcgg ctgaacacga caggcg 26

<210> SEQ ID NO 15
<211> LENGTH: 70
<212> TYPE: DNA
<213> ORGANISM: Artificial Sequence
<220> FEATURE:
<223> OTHER INFORMATION: Synthetic DNA Primer

<400> SEQUENCE: 15
atatggatcc tggaaaagcc cggggctctg gcaagagctt gctgtcctct gcatcaggcc 60
ccaggcccgg 70

<210> SEQ ID NO 16
<211> LENGTH: 44
<212> TYPE: DNA
<213> ORGANISM: Artificial Sequence
<220> FEATURE:
<223> OTHER INFORMATION: Synthetic DNA Primer

<400> SEQUENCE: 16
atatatatgg atccgggctg agggcatacg atggcttgtc tctg 44

<210> SEQ ID NO 17
<211> LENGTH: 61
<212> TYPE: DNA
<213> ORGANISM: Artificial Sequence
<220> FEATURE:
<223> OTHER INFORMATION: Synthetic DNA Primer

<400> SEQUENCE: 17
atatatatgc ggccgcctaa tgatgatgat gatgatgtgg gaactggggc actgtgccca 60
g 61

<210> SEQ ID NO 18
<211> LENGTH: 21
<212> TYPE: DNA
<213> ORGANISM: Artificial
<220> FEATURE:
<223> OTHER INFORMATION: Synthetic DNA Sense primer for GAPDH

<400> SEQUENCE: 18
cggagtcaac ggatttggtc g 21

<210> SEQ ID NO 19
<211> LENGTH: 21
<212> TYPE: DNA
<213> ORGANISM: Artificial
<220> FEATURE:
<223> OTHER INFORMATION: Synthetic DNA Antisense primer for GAPDH

<400> SEQUENCE: 19
agccttctcc atggtggtga a 21

<210> SEQ ID NO 20
<211> LENGTH: 20
<212> TYPE: DNA
<213> ORGANISM: Artificial
<220> FEATURE:
<223> OTHER INFORMATION: Synthetic DNA Sense primer for Nestin

<400> SEQUENCE: 20
cagcgttgga acagaggttg 20

<210> SEQ ID NO 21
<211> LENGTH: 20
<212> TYPE: DNA
<213> ORGANISM: Artificial
<220> FEATURE:
<223> OTHER INFORMATION: Synthetic DNA Antisense primer for Nestin

<400> SEQUENCE: 21
gctggcacag gtgtctcaag 20

<210> SEQ ID NO 22
<211> LENGTH: 22
<212> TYPE: DNA
<213> ORGANISM: Artificial
<220> FEATURE:
<223> OTHER INFORMATION: Synthetic DNA Sense primer for Slug

<400> SEQUENCE: 22
catctttggg gcgagtgagt cc 22

<210> SEQ ID NO 23
<211> LENGTH: 22
<212> TYPE: DNA
<213> ORGANISM: Artificial
<220> FEATURE:
<223> OTHER INFORMATION: Synthetic DNA Antisense primer for Slug

<400> SEQUENCE: 23
cccgtgtgag ttctaatgtg tc 22

<210> SEQ ID NO 24
<211> LENGTH: 20
<212> TYPE: DNA
<213> ORGANISM: Artificial
<220> FEATURE:
<223> OTHER INFORMATION: Synthetic DNA Sense primer for Sox9

<400> SEQUENCE: 24
gtcagccagg tgctcaaagg 20

<210> SEQ ID NO 25
<211> LENGTH: 20
<212> TYPE: DNA
<213> ORGANISM: Artificial
<220> FEATURE:
<223> OTHER INFORMATION: Synthetic DNA Antisense primer for Sox9

<400> SEQUENCE: 25
acttgtaatc cgggtggtcc 20

<210> SEQ ID NO 26
<211> LENGTH: 21
<212> TYPE: DNA
<213> ORGANISM: Artificial
<220> FEATURE:
<223> OTHER INFORMATION: Synthetic DNA Sense primer for Dermo-1

<400> SEQUENCE: 26
gcaagaagtc gagcgaagat g 21

<210> SEQ ID NO 27
<211> LENGTH: 21
<212> TYPE: DNA
<213> ORGANISM: Artificial

<220> FEATURE:
<223> OTHER INFORMATION: Synthetic DNA Antisense primer for Dermo-1

<400> SEQUENCE: 27
ggcaatggca gcatcattca g 21

<210> SEQ ID NO 28
<211> LENGTH: 21
<212> TYPE: DNA
<213> ORGANISM: Artificial
<220> FEATURE:
<223> OTHER INFORMATION: Synthetic DNA Sense primer for BMP-4

<400> SEQUENCE: 28
ttctgcagat gtttgggctg c 21

<210> SEQ ID NO 29
<211> LENGTH: 20
<212> TYPE: DNA
<213> ORGANISM: Artificial
<220> FEATURE:
<223> OTHER INFORMATION: Synthetic DNA Antisense primer for BMP-4

<400> SEQUENCE: 29
agagccgaag ctctgcagag 20

<210> SEQ ID NO 30
<211> LENGTH: 20
<212> TYPE: DNA
<213> ORGANISM: Artificial
<220> FEATURE:
<223> OTHER INFORMATION: Synthetic DNA Sense primer for Wnt-5a

<400> SEQUENCE: 30
ggatggctgg aagtgcaatg 20

<210> SEQ ID NO 31
<211> LENGTH: 20
<212> TYPE: DNA
<213> ORGANISM: Artificial
<220> FEATURE:
<223> OTHER INFORMATION: Synthetic DNA Antisense primer for Wnt-5a

<400> SEQUENCE: 31
acacaaactg gtccacgatc 20

<210> SEQ ID NO 32
<211> LENGTH: 20
<212> TYPE: DNA
<213> ORGANISM: Artificial
<220> FEATURE:
<223> OTHER INFORMATION: Synthetic DNA Sense primer for Versican

<400> SEQUENCE: 32
acgatgccta ctttgccacc 20

<210> SEQ ID NO 33
<211> LENGTH: 21
<212> TYPE: DNA
<213> ORGANISM: Artificial
<220> FEATURE:
<223> OTHER INFORMATION: Synthetic DNA Antisense primer for Versican

<400> SEQUENCE: 33
tagtgaaaca caaccccatc c 21

-continued

```
<210> SEQ ID NO 34
<211> LENGTH: 20
<212> TYPE: DNA
<213> ORGANISM: Artificial
<220> FEATURE:
<223> OTHER INFORMATION: Synthetic DNA Sense primer for CD133

<400> SEQUENCE: 34

atggccctcg tactcggctc                                              20


<210> SEQ ID NO 35
<211> LENGTH: 20
<212> TYPE: DNA
<213> ORGANISM: Artificial
<220> FEATURE:
<223> OTHER INFORMATION: Synthetic DNA Antisense primer for CD133

<400> SEQUENCE: 35

cacgcggctg taccacatag                                              20
```